US007531163B2

(12) United States Patent
Samadpour

(10) Patent No.: US 7,531,163 B2
(45) Date of Patent: May 12, 2009

(54) ENRICHMENT METHODS FOR THE DETECTION OF PATHOGENS AND OTHER MICROBES

(75) Inventor: Mansour Samadpour, Seattle, WA (US)

(73) Assignee: Institute for Environmental Health, Inc., Lake Forest Park, WA (US)

(*) Notice: Subject to any disclaimer, the term of this patent is extended or adjusted under 35 U.S.C. 154(b) by 0 days.

(21) Appl. No.: 10/848,253

(22) Filed: May 17, 2004

(65) Prior Publication Data

US 2004/0241644 A1 Dec. 2, 2004

Related U.S. Application Data

(60) Provisional application No. 60/470,975, filed on May 16, 2003.

(51) Int. Cl.
*A61K 49/00* (2006.01)
*C12Q 1/00* (2006.01)
*G01N 33/53* (2006.01)

(52) U.S. Cl. .................. 424/9.1; 424/130.1; 424/163.1; 424/164.1; 424/184.1; 424/234.1; 435/4; 435/7.2; 435/243

(58) Field of Classification Search .................. 424/9.1, 424/130.1, 163.1, 164.1, 184.1, 234.1; 435/4, 435/7.2, 243
See application file for complete search history.

(56) References Cited

U.S. PATENT DOCUMENTS 6,060,266 A * 5/2000 Naqui et al. .................. 435/34

OTHER PUBLICATIONS

Bacteriological Analytical Manual *Online*(U.S. Food & Drug Administration, Center for Food Safety & Applied Nutrition) Chapters 4, 4a, 5, 6, 7, 8, 9, 10.

Bhaduri, S. et al., Use of a Single Procedure for Selective Enrichment, Isolation, and Identification of Plasmid-Bearing Virulent *Yersinia enterocolitica* of Various Serotypes from Pork Samples, Applied and Environmental Microbiology 63:1657-1660, 1997.
Busch and Donnelly, Development of a Repair-Enrichment Broth for Resuscitation of Heat-Injured *Listeria monocytogenes* and *Listeria innocua*, Applied and Environmental Microbiology 58:14-20, 1992.
Dahlenborg, M. et al., Development of a Combined Selection and Enrichment PCR Procedure for *Clostridium botulinum* Types B, E, and F and Its Use to Determine Prevalence in Fecal Samples from Slaughtered Pigs, Applied and Environmental Microbiology 67:4781-4788, 2001 1987.

Doyle and Schoeni, Isolation of *Escherichia coli* O157:H7 from Retail Fresh Meats and Poultry, Applied and Environmental Microbiology 53:2394-2396, 1987.
Fach, P. et al., PCR and Gene Probe Identification of Botulinum Neurotoxin A-, B-, E-,F-, and G-Producing *Clostridium* spp. and Evaluation in Food Samples, Applied and Environmental Microbiology 61:389-392, 1995.
Ng, S.P. et al., Detection and Serogroup Differentiation of *Salmonella* spp. in Food within 30 Hours by Enrichment-Immunoassay with a T6 Monoclonal Antibody Capture Enzyme-Linked Immunosorbent Assay, Applied and Environmental Microbiology 62:2294-2302, 1996.
Norton et al., Molecular Studies on the Ecology of *Listeria monocytogenes* in the Smoked Fish Processing Industry, Applied and Environmental Microbiology 67:198-205, 2001.
Padhye and Doyle, Rapid Procedure for Detecting Enterohemorrhagic *Escherichia coli* O157:H7 in Food, Applied and Environmental Microbiology 57:2693-2698, 1991.
Pignato, S. et al., Evaluation of New Culture Media for Rapid Detection and Isolation of *Salmonella* in Foods, Applied and Environemtal Microbiology 61:1996-1999, 1995.
Ryser, E.T. et al., Recovery of Different *Listeria* Ribotypes from Naturally Contaminated, Raw Refrigerated Meat and Poultry Products with Two Primary Enrichment Media, Applied and Environmental Microbiology 62:1781-1787, 1996.
Zhao et al., Prevalence of Enterohemorrhagic *Escherichia coli* O157:H7 in a Survey of Dairy Herds, Applied and Environmental Microbiology 61:1290-1293, 1995.

* cited by examiner

*Primary Examiner*—Rodney P. Swartz
(74) *Attorney, Agent, or Firm*—Barry L. Davison, J.D.; Davis Wright Tremaine LLP

(57) ABSTRACT

The present invention provides novel enrichment, testing and detection methods for detection of pathogens or other microbes in a food, water, wastewater, industrial, pharmaceutical, botanical, environmental samples and other types of samples analyzed by enrichment-detection methods. In preferred aspects, a sample is obtained at a first location and is diluted (e.g., in the case of a solid or semi-solid sample or liquid) at the first location at a ratio of about 1:0 (wt./vol.) to 1:2 (wt./vol.), or greater, preferably at a ratio of about 1:0.1 (wt./vol.) or greater, or more preferably, at a ratio of about 1:2 (wt./vol.) or greater. The diluted sample is incubated at an optimal temperature in an incubator and either tested locally, or sent in a shipping incubator to a second location that is a remote test location. The incubated sample is received and tested at the second location by assaying the sample, or a portion thereof, with an assay suitable to detect the pathogen or other microbe. In alternate embodiments, no dilution at the first location is required, and optionally minimal additions to adjust intrinsic deficiencies may be made, but the sample is nonetheless incubated during transit to the test location.

23 Claims, 11 Drawing Sheets

ENRICHMENT METHODS FOR THE DETECTION OF PATHOGENS AND OTHER MICROBES

CROSS-REFERENCE TO RELATED APPLICATIONS

Figure 1:
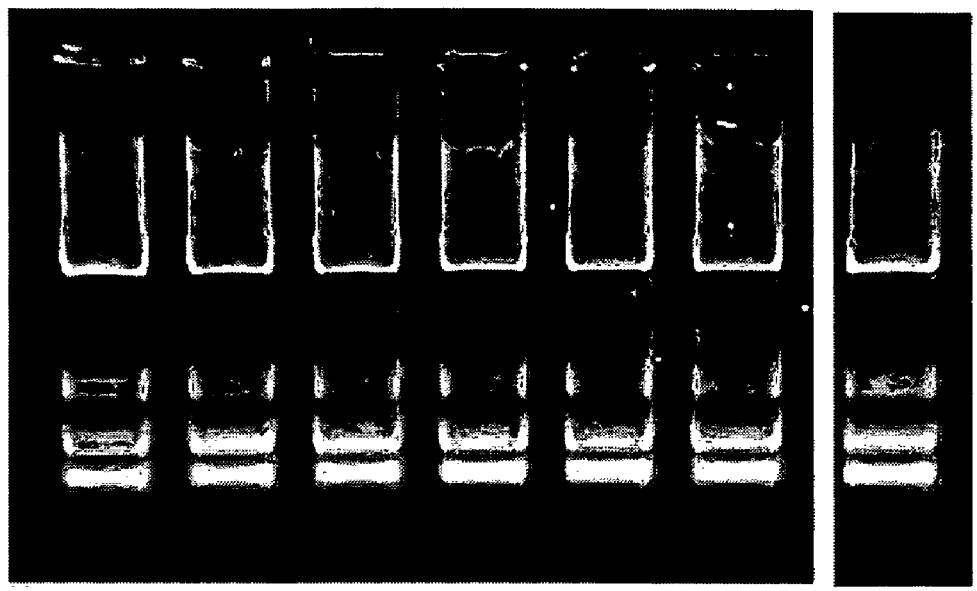

This application claims the benefit of priority to U.S. Provisional Application No. 60/470,975, filed 16 May 2003 and entitled "DRY AND SEMIDRY ENRICHMENT FOR THE DETECTION OF FOODBORNE PATHOGENS," incorporated by reference herein in its entirety.

FIELD OF THE INVENTION

The present invention, in various aspects, relates generally to improving the efficiency of producing foods, and the safety and quality of food products, including but not limited to beef, pork, sheep, bison, deer, elk, poultry (e.g., chicken and turkey) and fish, produce, juices, dairy products, dry goods (cereals, etc), and all manners of raw and processed foods, environmental samples (water, wastewater, soil, surface samples, samples taken by impingers and filtration, etc), pharmaceuticals, and other types of samples that are to be analyzed using enrichment-detection protocols. More specifically, embodiments of the present invention relate to novel methods for pathogen testing and detection at a site that is remote from a site of which samples are taken.

BACKGROUND

Most regulatory agencies require, and customers demand specific testing for pathogens that are common to specific food types, and agricultural products, that are capable of in vivo multiplication. Rapid and accurate methods for detection of foodborne and waterborne pathogens are essential, particularly in the context of food manufacturing processes, pharmaceutical industry, drinking water and wastewater utilities, management of fisheries resources and bodies of water (recreational, etc). The same applies to the general detection of human, animal and plant pathogens, and in general to any kind of bacterial, viral, fungal, and parasitic pathogens that are capable of in vivo multiplication, and their indicator organisms. Many manufacturers and utilities have, consequently, had to build in-house labs to expedite the testing, or lose valuable time waiting for test results when samples are shipped out to outside labs. The same is true for the utility industry (water and wastewater, and the pharmaceutical industry. Furthermore, using art-recognized and current standard methods, the cost of enrichment media used to expand the numbers of one or more particular pathogens to detectable levels, can be substantial.

Prior art enrichment methods. Significantly, conventional/ standard methods for detection of pathogens in food (dry and liquid) involve diluting the sample 1:10 (wt/v) with media (e.g., sterile media) (or with another diluent, followed immediately by serial dilution into media to provide an effective 1:10 dilution into media), and thus involve the use of substantial volumes of media. For example, the conventional method for expanding and testing for coliforms, fecal coliforms and *E. Coli* in food, comprises a 1:10 dilution of the samples (e.g., 50 g into 450 ml) (see, e.g., U.S. FDA Bacteriology Analytical Manual Online, Chapter 4 and 4A, describing standard 1:10 dilution procedures for testing of coliforms, fecal coliforms and *E. Coli* in food, shellfish and juices). Significantly, these protocols have been adopted in the field so that samples (e.g., meat samples) at remote locations are typically diluted 1:10 (wt./vol.), and then shipped under ambient or uncontrolled conditions to a test location, where they are incubated at an optimal temperature and subsequently tested for pathogens.

For example, the following prior art examples comprise enrichment followed by detection of the target organisms in the enriched media, and are based on the use of 1:10 dilution of the sample in an appropriate media/buffer:

*Escerichia coli*. The assay for the detection of *E. coli* in citrus juices, as described in the Bacteriological Analytical manual (BAM) (United States Food & Drug Administration, and Center for Food Safety & Applied Nutrition, Bacteriological Analytical Manual, Chapter 4, Enumeration of *Escerichia coli* and the Coliform Bacteria, September 2002), is carried out in duplicate. Basically, a 10-mL portion of juice is aseptically inoculated into 90 mL of Universal Pre-enrichment Broth (UPEB) and incubated at 35° C. for 24 h. After enrichment, the sample is mixed and 1 mL is transferred from each UPEB enrichment broth into 9 mL of EC broth containing a CC disc, and EC/CC broth tubes are incubated at 44.5° C. in a circulating water bath for 24 h. Preferably, positive (tube inoculated with a MUG (+) *E. coli* strain) and negative (tube inoculated with *K. pneumoniae*) controls are included. The tubes are checked in the dark and under long wave UV light. The presence of blue fluorescence in either tube is indicative that *E. coli* is present in the sample. Note: the CC discs also contain X-gal, which when cleaved by β-galactosidase will yield blue color on or around the disc. This reaction is analogous to measuring acid/gas production from fermentation of lactose hence, the presence of blue color is indicative of coliforms. For the detection of *Escerichia coli* O157:H7 in food, 25 g of ground beef is incubated in 225 ml of selective enrichment medium for 16 to 18 h at 37° C. with agitation (Padhye & Doyle, *Appl. Environ. Microbiol.* 57:2693-2698, 1991). Enzyme-linked immunosorbent assay (ELISA) is used to detect the pathogen from the enriched culture. Doyle & Schoeni (*Appl. Environ. Microbiol.* 53:2394-2396, 1987.) isolated *E. coli* O157:H7 from retail fresh meats and poultry using the enrichment method whereby 25 g of food sample was added to 225 modified TSB. In the same fashion, fecal sample enrichment was done with modified TSB at 1:10 ratio (Zhao et al., *Appl. Environ. Microbiol.* 61:1290-1293, 1995).

*Salmonella*. BAM, 2003 teaches use of 1:9 sample/broth ratio (1:10 dilution) for detection of *salmonella* in meats, meat substitutes, meat by-products, animal substances, glandular products, and meals (fish, meat, bone). The recommended procedure is as follows: weigh twenty-five gm (25 g) of sample aseptically; add 225 ml of sterile lactose broth and blend for two min.; transfer the homogenized mixture aseptically to a sterile wide-mouth, screw-cap jar (500 ml) or other appropriate container and let stand 60+5 min at room temperature with the container securely capped (blending can be omitted if mixture is powder, ground or comminuted) (lactose broth is added to samples that do not require blending); mix well and check the pH with the help of a test paper; adjust pH, if necessary, to 6.8±0.2; add up to 2.25 ml steamed (15 min) Tergitol Anionic 7 and mix well (alternatively, steamed (15 min) Triton X-100 can be used) (the use of surfactants should be limited to initiate foaming); and loosen jar caps ¼ turn and incubate sample mixtures 24±2 h at 35° C.

Likewise, Pignato et al. (*Appl. Environ. Microbiol.* 61: 1996-1999, 1995) evaluated new culture media for rapid detection and isolation of salmonellae in foods. The methodology followed was as follows: fifty g of meat samples are taken and minced; 25 g is homogenized for 1 min in a stomacher with 225 ml of Buffered Peptone Water (BPW) and then pre-enriched by incubation for 24 h at 37° C., while 25 g is homogenized with 225 ml of Salmosyst broth and is further pre-enriched by incubation for 6 h at 37° C.; the whole contents of two eggs are homogenized for 30 s in a stomacher and then divided in two aliquots of 50 g each for pre-enrichment with 450 ml of BPW and 450 ml of Salmosyst broth; and an aliquot of 10 ml of BPW is transferred to 100 ml of Müller-Kauffmann tetrathionate broth (M-KTB), for selective enrichment by incubation for 24 and 48 h at 43° C. after the preenrichment. For the detection of *Salmonella* spp., 25 g of ground pork is enriched in 225 ml of prewarmed buffered peptone water (Ng et al., *Appl. Environ. Microbiol.* 62:2294-2302, 1996). The same ratio (1:10) of enrichment was done for infant milk for the detection of *Salmonella* spp.

See also United States Food & Drug Administration, and Center for Food Safety & Applied Nutrition. Bacteriological Analytical Manual. Chapter 6. *Salmonella*, April 2003.

*Shigella sonnei*. The conventional culture method for the enrichment of *Shigella sonnei* includes the use of 25 g sample into 225 ml shigella broth, already containing 0.5 μg/ml novobiocin (United States Food & Drug Administration, and Center for Food Safety & Applied Nutrition, Bacteriological Analytical Manual. Chapter 6. *Shigella*, January 2001). The procedure is as follows: pour supernatant into sterile 500 ml Erlenmeyer flask; adjust pH, to 7.0±0.2 with sterile 1 N NaOH or 1 N HCl; set the flask in an anaerobic jar with fresh catalyst; insert GasPak™ and activate by adding water; incubate the jars in 44.0° C. water bath for 20 h; stir the enrichment culture suspension and streak on a MacConkey agar; and incubate for 20 h at 35° C.

*Campylobacter*. United States Food & drug Administration, and Center for Food safety & Applied Nutrition, Bacteriological Analytical Manual. Chapter 7, *Campylobacter*, March 2001 (2001) suggests the use of a 1:10 dilution for sample enrichment when high numbers of background flora (with broad species diversity) are present. It is taught that sample dilution helps antibiotics perform more effectively, and *campylobacter* cells utilize the low-oxygen atmosphere more efficiently.

*Listeria*. For the prior art enrichment of *Listeria monocytogenes* in composite samples, a composite blend of 50 g (equivalent to 25 g food plus 25 ml basal Buffered *Listeria* enrichment broth (BLEB)) is mixed with a 200 ml amount of basal BLEB. An aliquot (50 ml) of the composite blend is retained, preferably at 5° C. and not below 0° C., for possible pathogen enumeration. For non-composited samples, single 25-g analytical portions of food are blended or stomached in 225 ml of basal BLEB and pre-enriched/enriched as per the procedures. A 25-g sample is retained for possible pathogen enumeration and should be stored either frozen, in a non-defrosting freezer or at 5° C.

Ryser et al (*Appl. Environ. Microbiol.* 62(5): 1781-1787, 1996) conducted experiments for the recovery of *Listeria* ribotypes from naturally contaminated, raw refrigerated meat and poultry products. A 1:10 sample dilution is used. Paired samples of ground beef, pork sausage, ground turkey, and chicken weighing 25 g are inoculated into 225 ml each of University of Vermont-modified *Listeria* enrichment broth (UVM; Difco Laboratories, Detroit, Mich.) and *Listeria* repair broth (LRB; developed by Busch and Donnelly; Busch & Donnelly, *Appl. Environ. Microbiol.* 58:14-20, 1992), homogenized for 2 min in a Lab-Tek 400 Stomacher (Tekmar, Cincinnati, Ohio), and incubated at 30° C. An aliquot of 0.1 ml of each UVM and LRB primary enrichment is inoculated into a separate tube containing 10 ml of Fraser broth after an incubation of 22 to 26 h at 30° C. Following 24 and 40 h of incubation at 35° C., all secondary enrichments, regardless of color change due to esculin hydrolysis, are streaked onto modified Oxford agar plates. All plates are incubated at 35° C. for 24 h, after which two presumptive *Listeria* isolates per sample for each primary enrichment medium are streaked onto brain heart infusion agar plates for purification and incubated at 35° C. for 24 h. An additional eight presumptive UVM and LRB *Listeria* isolates per primary enrichment medium from five samples of each of the four products are also streaked onto plates of brain heart infusion agar and similarly incubated.

Likewise, Norton et al. (*Appl. Environ. Microbiol.* 67(1): 198-205, 2001) use a dilution of 1:10 for the *Listeria* enrichment. Twenty-five-gram portions of raw, in-process, and smoked fish are homogenized in 225 ml of *Listeria* Enrichment Broth (LEB) (Difco Laboratories, Detroit, Mich.) using a Stomacher 400 laboratory blender (Seward Ltd.). Brine solutions, in 25-ml aliquots, are inoculated into 225 ml of LEB. Swabs and transport media are transferred aseptically to 8 ml of LEB. After 24 and 48 h of incubation at 30° C., 0.1 ml of each enrichment culture are plated on Oxford medium containing the Oxford Antimicrobic Supplement (Difco Laboratories), and incubated at 30° C. for 48 h. Pure culture isolates used for hlyA PCR or BAX system analysis (for confirmation that this system correctly identifies isolates from culture-positive, BAX system-negative samples) are cultured into brain heart infusion broth at 37° C. with shaking for 12 to 15 h.

Growth of healthy and heat-injured strains of *Listeria monocytogenes* and *Salmonella* spp. from raw milk was supported by enrichment of sample in the universal pre-enrichment broth. One ml of milk was inoculated into tubes containing 9 ml of pre-enrichment broth (Jiang et al., *J. Dairy Sci.* 81:7298-72830, 1998).

See also United States Food & Drug Administration, and Center for Food Safety & Applied Nutrition. Bacteriological Analytical Manual, Chapter 10. Detection and enumeration of *Listeria monocytogenes* in foods, January 2003.

*Yersinia enterocolitica* and *Yersinia pseudotuberculosis*. The simplified procedure for isolating *Yersinia* from food, water, and environmental samples as suggested in Bacteriological Analytical Manual (United States Food & Drug Administration, and Center for Food Safety & Applied Nutrition, 2001) is as follows: aseptically weigh 25 g sample into 225 ml Peptone sorbitol bile broth (PSBB). Homogenize for 30 s and incubate at 10° C. for 10 days. If high levels of *Yersinia* are expected in product, spread-plate 0.1 ml on MacConkey agar (Doyle et al., *Appl. Environ. Microbiol.* 42:661-666, 1981, In United States Food & Drug Administration, and Center for Food Safety & Applied Nutrition, 2001, Weissfeld (Weissfeld & Sonnenwirth, *J. Clin. Microbiol.* 15:508-510, 1982.) In United States Food & Drug Administration, and Center for Food Safety & Applied Nutrition, 2001) and 0.1 ml on CIN agar (Schiemann, D. A., *Appl. Environ. Microbiol.* 43:14-27, In United States Food & Drug Administration, and Center for Food Safety & Applied Nutrition. January 2001, Bacteriological Analytical Manual. Chapter 8, 1982, In United States Food & Drug Administration, and Center for Food Safety & Applied Nutrition, 2001; Schiemann & Wauters, *Yersinia*. Chapter 27. *Yersinia pseudotuberculosis*, pp. 601-672, In: Compendium of Methods for the Microbiological Examination of Foods, 3rd ed., C. Vanderzant and D. F. Splittstoesser (eds), American Public Health Association, Washington, D.C., In United States Food & Drug Administration, and Center for Food Safety & Applied Nutrition. January 2001, Bacteriological Analytical Manual, Chapter 8, 1992; In United States Food & Drug Administration, and Center for Food Safety & Applied Nutrition) before incubating the broth.

A selective enrichment for plasmid-bearing virulent serotypes of *Yersinia enterocolitica* from pork was developed in which 10 g of samples is incubated with 90 ml of modified Tripticase soy broth (MTSB) (Bhaduri S. et al., *Appl. Environ. Microbiol*. 63(5):1657-60, 1997). The first 10 ml of MTSB is added to the samples and was allowed to stand for 5 min, followed by adding the remainder 80 ml of MTSB into the sample bag for a 24 h incubation at 12° C.

*Vibrio cholerae*. Bacteriological Analytical manual (United States Food & Drug Administration, and Center for Food Safety & Applied Nutrition, Bacteriological Analytical Manual, Chapter 9; Vibrio, July 2001) recommends addition of 225 ml alkaline peptone water (APW) with 25 g of weighed sample into a tarred jar (approximately 500 ml capacity). Seafood or vegetables are blended or cut into small pieces with sterile scissors. The mixed sample is blended for 2 min at high speed, and incubated in APW at 35±2° C. for 6 to 8 h.

*Clostridium*. Fach et al. (*Appl. Environ. Microbiol*. 61:389-92, 1995) incubate 10 g of food samples (raw/cooked beef, raw/cooked pork, and raw fish) in 90 ml of Trypticase yeast extract glucose for the detection of *Clostridium* spp. Similarly, Dahlenborg et al. (*Appl. Environ. Microbiol*. 67:4781-8, 2001) incubate 10 g of feces in 90 ml of tryptone-peptone-glucose-yeast extract to select for *C. botulinum*.

Specilaized, selective media. Additionally, various specialized selection media (and agar) are known and used in the art. Such media comprises one or more anti-microbial reagents (e.g., tellurite and cefixime that selectively suppress particular (e.g., normal) flora growth and interference therefrom, to enhance the ability to detect, for example a slower growing pathogen (e.g., *E. coli* O157:H7). Such anti-microbial reagents, while having utility, nonetheless add even more expense to the media.

Therefore, not only is the cost of the sterile media itself significant, but, given the volumes typically involved, the associated shipping costs are also substantial given the large volumes (sample plus media/buffer). Furthermore, the size of the prior art samples (plus media/buffer) make it impractical to ship at an appropriate or optimal temperature (e.g. using temperature-controlled, spill-proof shipping containers/incubators. The inability to take advantage of shipping time for enrichment results in a substantial time delay in obtaining laboratory results. This has forced many industries and entities to either use local testing facilities, build in -house certifiable testing labs, or accept, a substantial expense, the additional 1-2 days of 'process' time while awaiting test results.

Generally speaking, development of more timely and cost effective sampling, enrichment and testing procedures will make efficient use of the industry's financial resources, and thus will facilitate industry implementation of, and compliance with regulatory guidelines.

Therefore, to provide efficient and cost effective testing methods, and to facilitate industry implementation of and compliance with regulatory guidelines, there is a pronounced need in the art for rapid and efficient methods and apparatus for detection, at test locations that are remote from the site(s) of sampling, of various kinds of bacterial, viral, fungal, and parasitic pathogens that are capable of in vivo multiplication.

There is a pronounced need in the art to reduce the time required to obtain meaningful test results from remote test locations.

There is a pronounced need in the art to reduce the costs of obtaining such timely meaningful test results from remote test locations.

There is a pronounced need in the art for accurate and efficient methods for testing samples at a remote location, including but not limited to beef, pork, sheep, bison, deer, elk, poultry (e.g., chicken and turkey) and fish, produce, juices, dairy products, dry goods (cereals, etc), and all manners of raw and processed foods, environmental samples (water, wastewater, soil, surface samples, samples taken by impingers and filtration, etc), pharmaceuticals, and other types of samples that are to be analyzed using enrichment-detection protocols.

SUMMARY OF THE INVENTION

The present invention provides novel enrichment, testing and detection methods for detection of pathogens or other microbes in food, water, wastewater, sludge, pharmaceutical, industrial samples, and the like. The methods are also applicable to testing samples including, but are not limited to beef, pork, sheep, bison, deer, elk, poultry (e.g., chicken and turkey) and fish, produce, juices, dairy products, dry goods (cereals, etc), and all manners of raw and processed foods, environmental samples (water, wastewater, soil, surface samples, samples taken by impingers and filteration, etc), pharmaceuticals, and other types of samples that are to be analyzed using enrichment-detection protocols.

In preferred aspects, a sample is obtained at a first location and is enriched, based on its intrinsic properties (if water activity and nutrition s, pH, are sufficient/proper to support the growth of the target organism), either with no addition of other compounds, or by the addition of minimal amounts of enrichment appropriate media, ranging from 0.1 volume to 1 volume(per wt sample). The samples are then incubated at the appropriate temperature which is selected on the basis of the temperature that allows for the optimal growth of the target organism (s) over the background flora. The samples, after sufficient incubation, are then analyzed for the presence of the pathogen using any number of available methods. Alternatively the enriched samples are incubated at an optimal temperature in an incubator during transit of the diluted sample to a second location that is a remote test location. The enriched, incubated sample is received and tested at the second location by assaying the received sample, or a portion thereof, with an assay suitable to detect the pathogen/target microbes.

In alternate preferred embodiments (e.g., liquid samples, juice, etc.), samples are enriched by adjusting their water activity (using sterile water/buffer/enrichment media), nutrient levels, pH, buffering capacity, and possibly addition of selective compounds (that repress the growth of competitive organisms in the samples) to the level that allows for the growth of the target organism, at the first location, followed by incubation and testing at the first location or shipping in transport incubators to a second testing location. The novel methods provide accurate, cost effective, and timely sampling and testing methods in-house or under circumstances where shipping of the sample to a remote testing location is required or desirable.

BRIEF DESCRIPTION OF THE DRAWINGS

FIGS. 1 and 2 show amplification products obtained by multiplex PCR of *E. coli* O157:H7 inoculated on meat trimmings incubated with a standard method (FIG. 1), or an embodiment of the inventive 'dry' method (FIG. 2) for 6 h, and concentrated by Dynabeads®. Numbers 1, 2, 3 were inoculation levels at $2.4\times10^1$, $0.36\times10^1$, and $0.036\times10^1$ CFU/g of meat, respectively. A and B were duplicate samples.

FIGS. 3 and 4 show amplification products obtained by multiplex PCR of *E. coli* O157:H7 inoculated on meat trimmings incubated with a standard method (FIG. 3), or an embodiment of the inventive 'dry' method (FIG. 4), for 7 h, and concentrated by Dynabeads®. Numbers 1, 2, 3 were inoculation levels at $2.4\times10^1$, $0.36\times10^1$, and $0.036\times10^1$ CFU/g of meat, respectively. A and B were duplicate samples.

Figure 5:
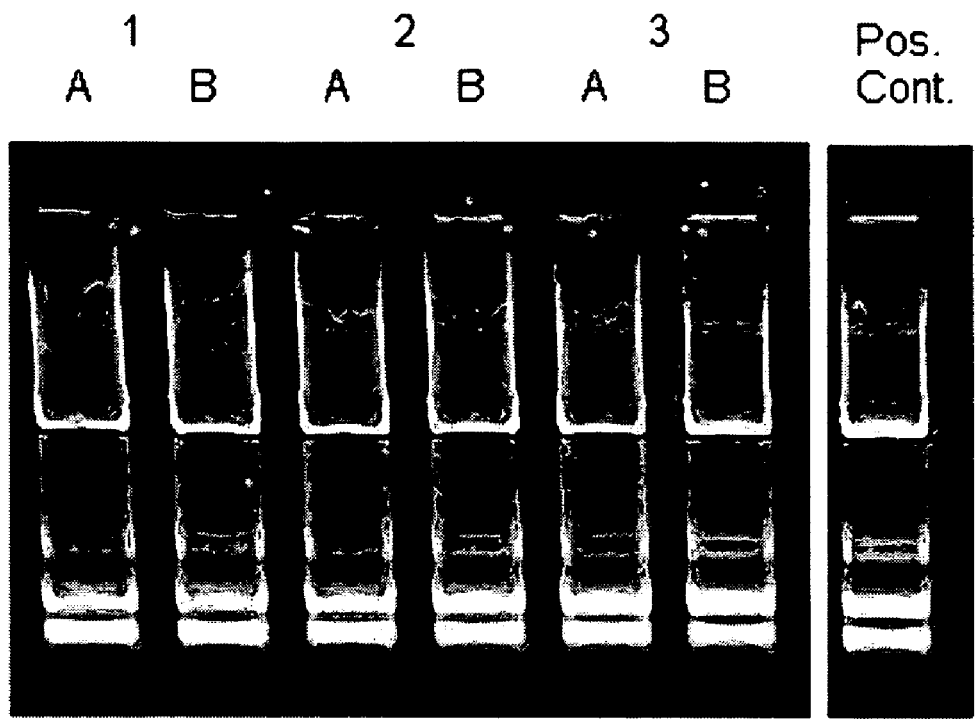
Figure 6:
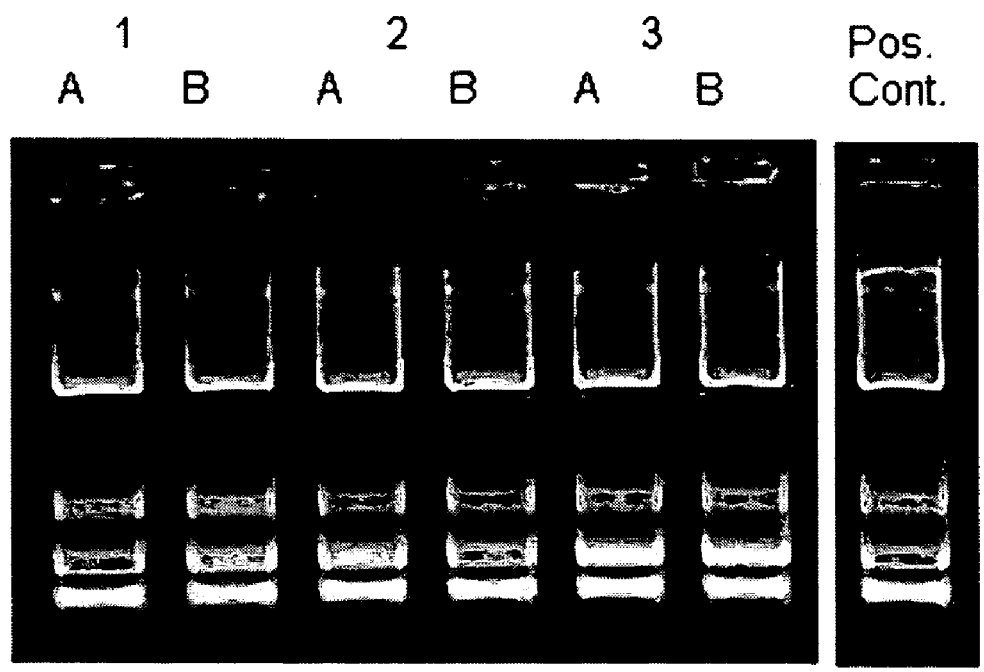

FIGS. 5 and 6 show amplification products obtained by multiplex PCR of *E. coli* O157:H7 inoculated on meat trimmings incubated with a standard method (FIG. 5), or an embodiment of the inventive 'dry' method (FIG. 6), for 8 h, and concentrated by Dynabeads®. Numbers 1, 2, 3 were inoculation levels at $2.4\times10^1$, $0.36\times10^1$, and $0.036\times10^1$ CFU/g of meat, respectively. A and B were duplicate samples.

Figure 7:
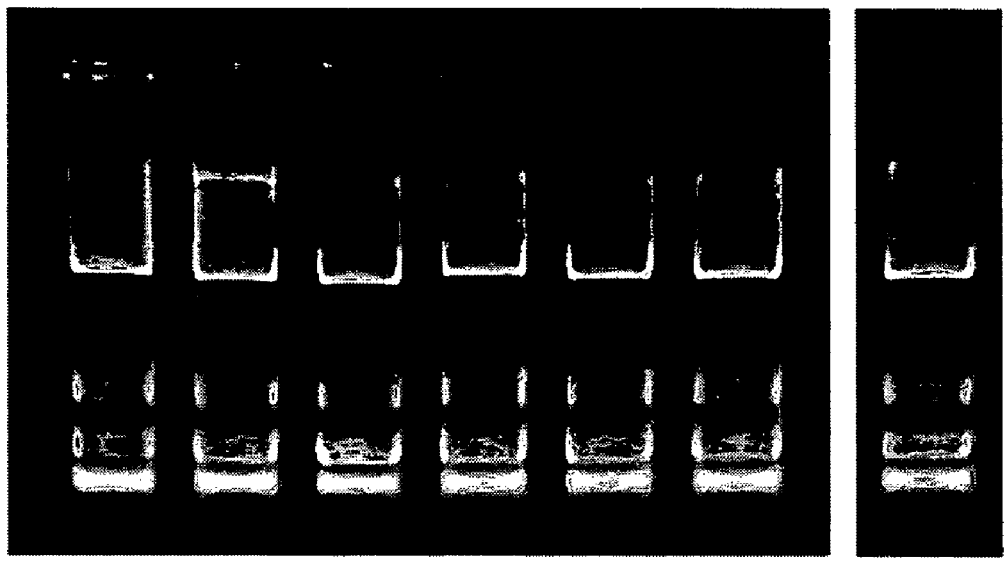
Figure 8:
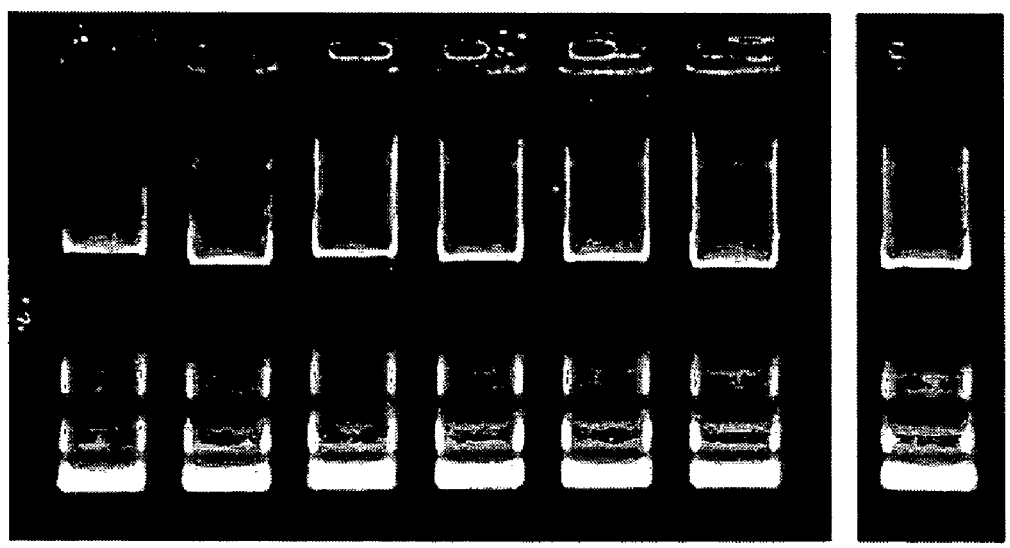

FIGS. 7 and 8 show amplification products obtained by multiplex PCR of *E. coli* O157:H7 inoculated on meat trimmings incubated with a standard method (FIG. 7), or an embodiment of the inventive 'dry' method (FIG. 8), for 6 h. Numbers 1, 2, 3 were inoculation levels at $2.4\times10^1$, $0.36\times10^1$, and $0.036\times10^1$ CFU/g of meat, respectively. A and B were duplicate samples.

Figure 9:
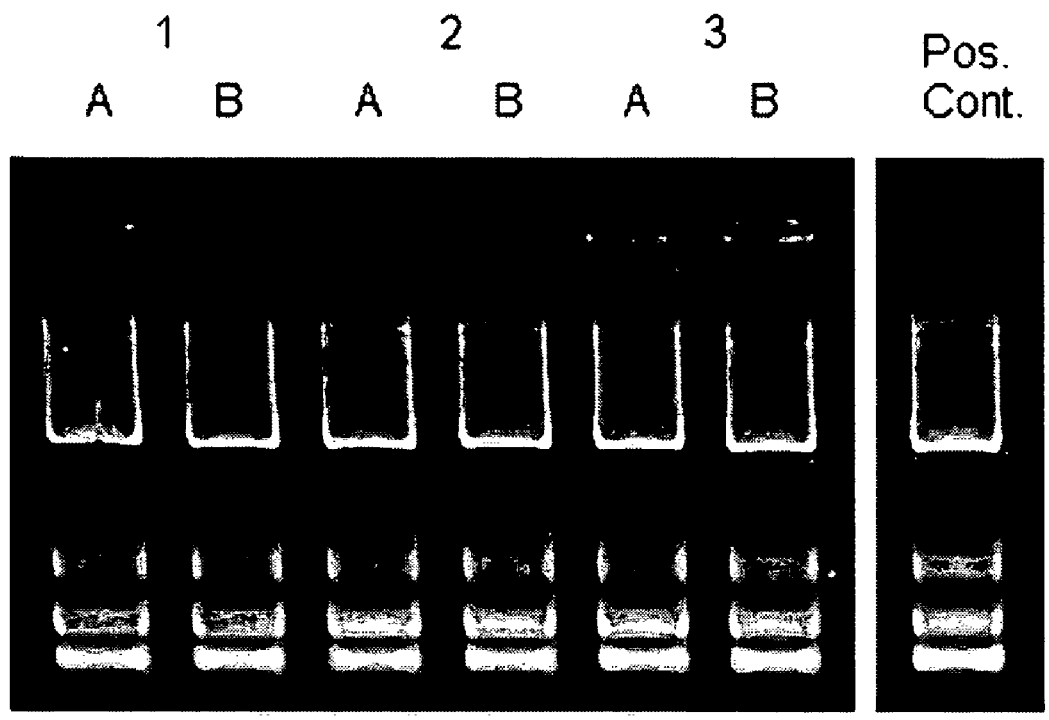
Figure 10:
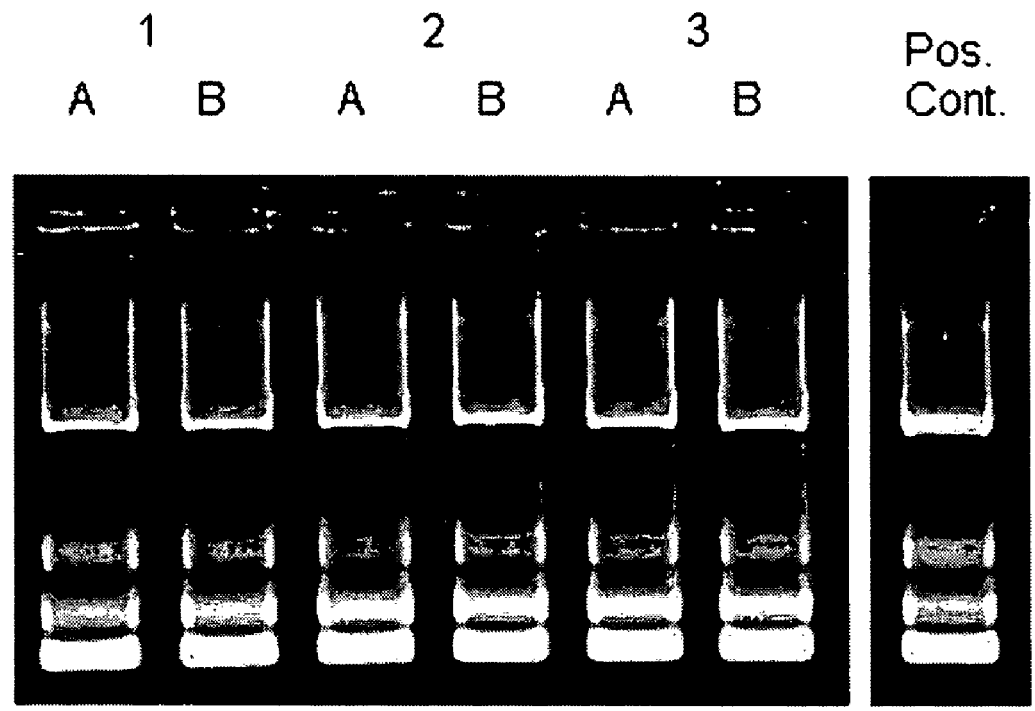

FIGS. 9 and 10 show amplification products obtained by multiplex PCR of *E. coli* O157:H7 inoculated on meat trimmings incubated with a standard method (FIG. 9), or an embodiment of the inventive 'dry' method (FIG. 10), for 7 h. Numbers 1, 2, 3 were inoculation levels at $2.4\times10^1$, $0.36\times10^1$, and $0.036\times10^1$ CFU/g of meat, respectively. A and B were duplicate samples.

Figure 11:
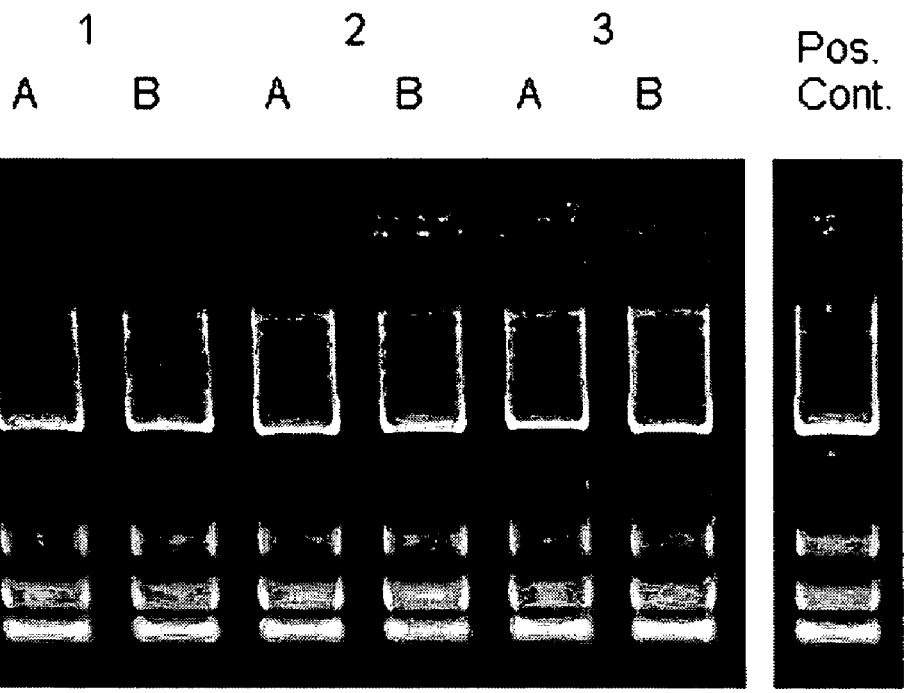
Figure 12:
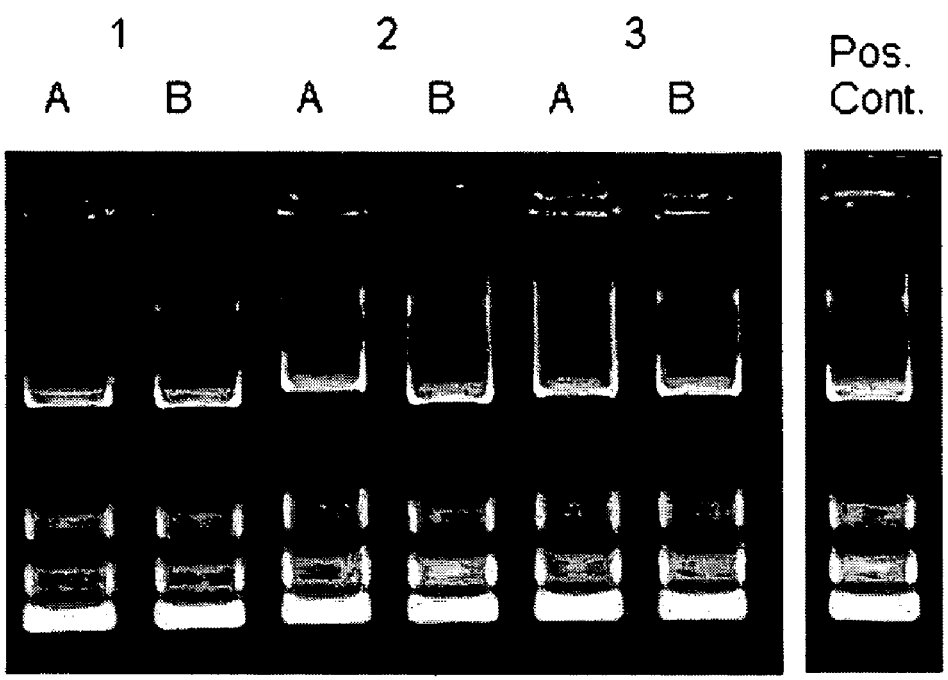

FIGS. 11 and 12 show amplification products obtained by multiplex PCR of *E. coli* O157:H7 inoculated on meat trimmings incubated with a standard method (FIG. 11), or an embodiment of the inventive 'dry' method (FIG. 12), for 8 h. Numbers 1, 2, 3 were inoculation levels at $2.4\times10^1$, $0.36\times10^1$, and $0.036\times10^1$ CFU/g of meat, respectively. A and B were duplicate samples.

Figure 13:
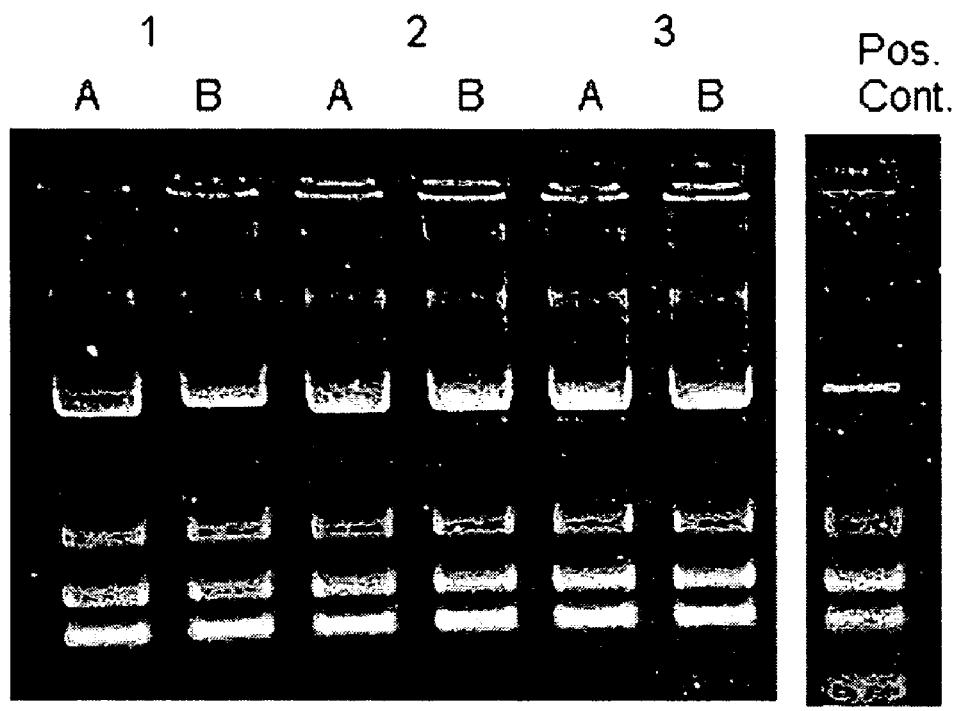
Figure 14:
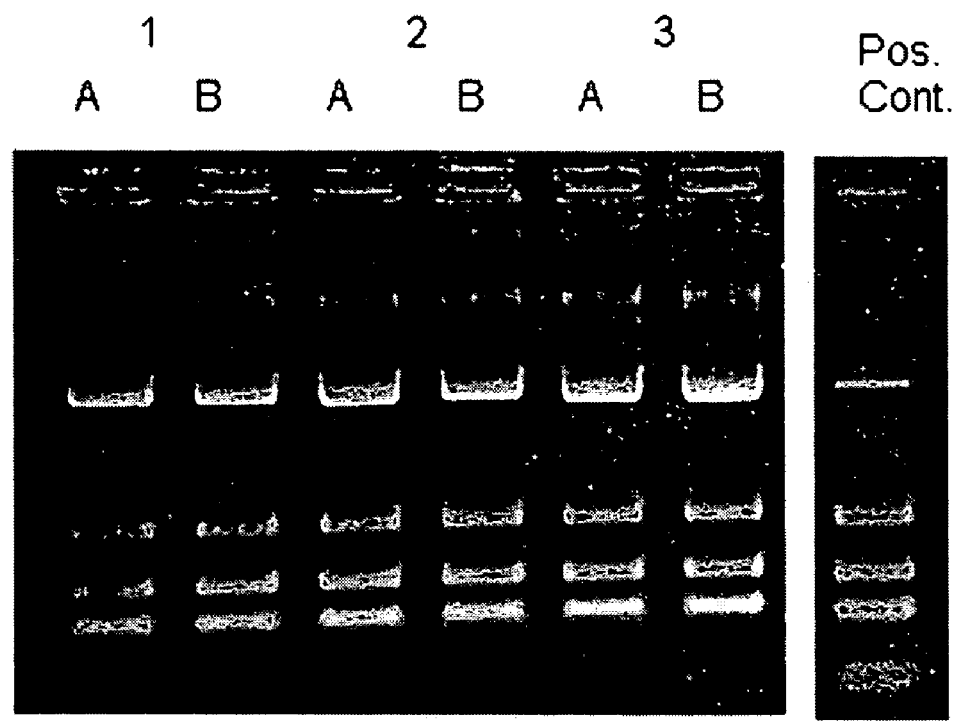

FIGS. 13 and 14 show amplification products obtained by multiplex PCR of *E. coli* O157:H7 inoculated on meat trimmings incubated with a standard method (FIG. 13), or an embodiment of the inventive 'dry' method (FIG. 14), for 24 h. Numbers 1, 2, 3 were inoculation levels at $2.4\times10^1$, $0.36\times10^1$, and $0.036\times10^1$ CFU/g of meat, respectively. A and B were duplicate samples.

Figure 15:
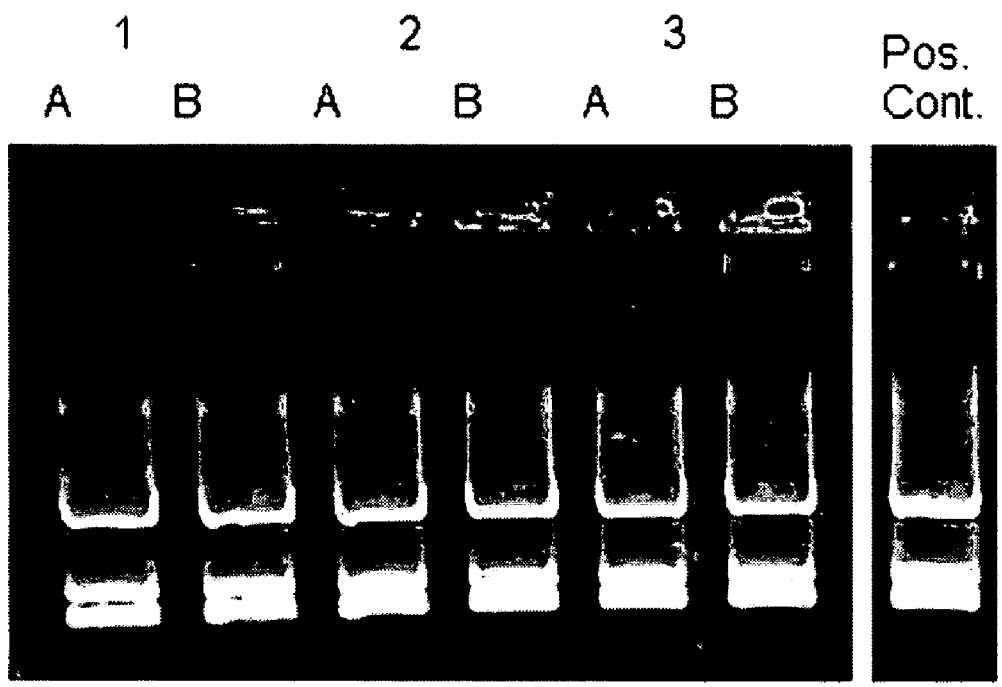
Figure 16:
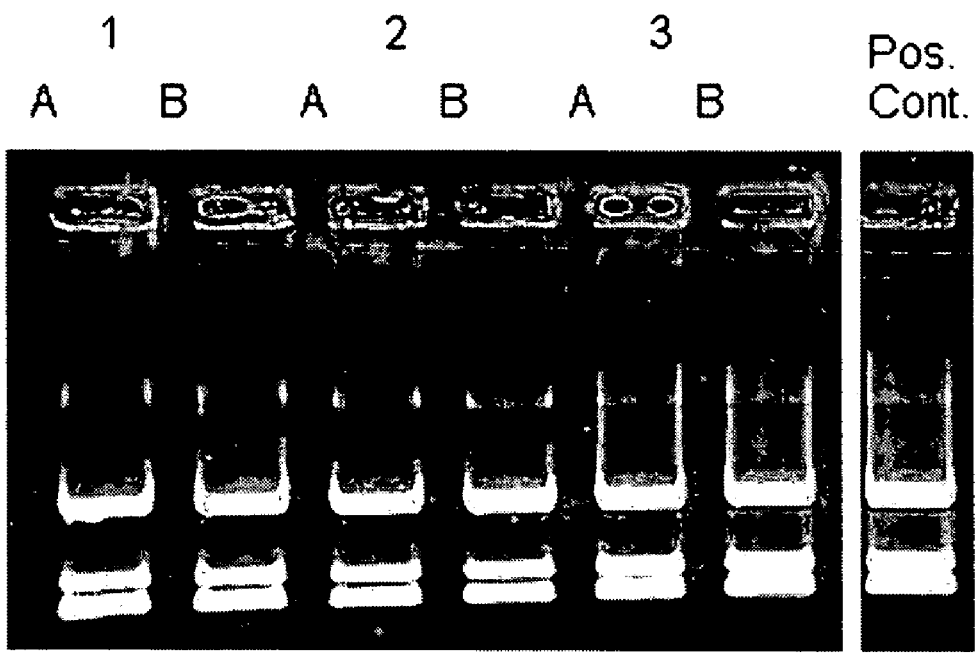

FIGS. 15 and 16 show amplification products obtained by multiplex PCR of *Salmonella* spp. inoculated on meat trimmings incubated with a standard method (FIG. 15), or an embodiment of the inventive 'dry' method (FIG. 16), for 6 h. Numbers 1, 2, 3 were inoculation levels at $1.6\times10^1$, $0.24\times10^1$, $0.042\times10^1$ CFU/g of meat, respectively. A and B were duplicate samples.

Figure 17:
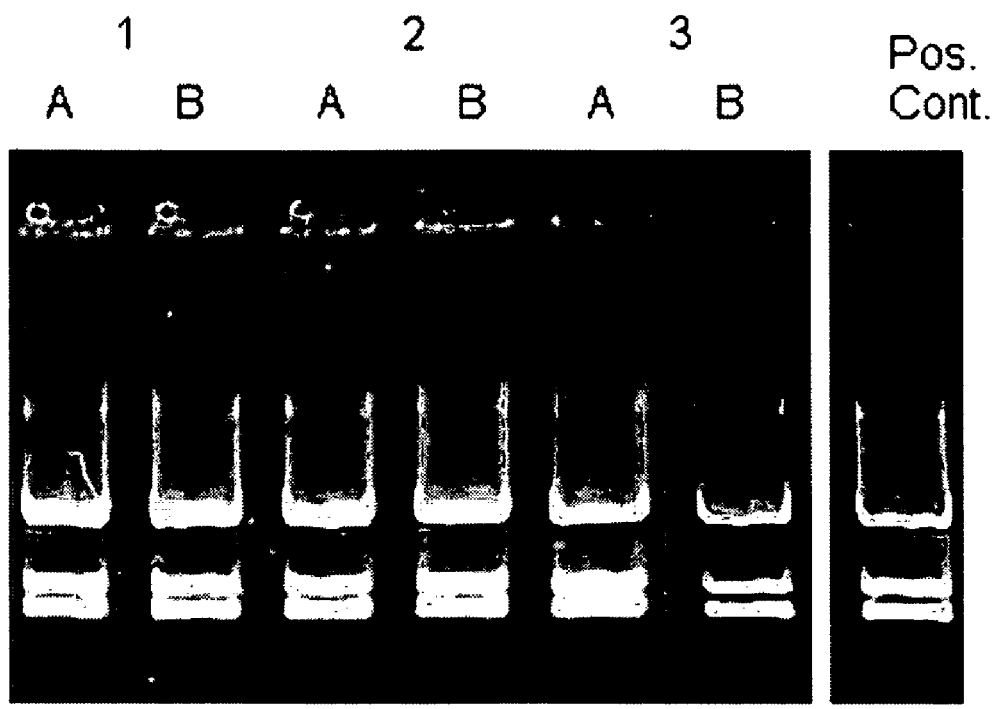
Figure 18:
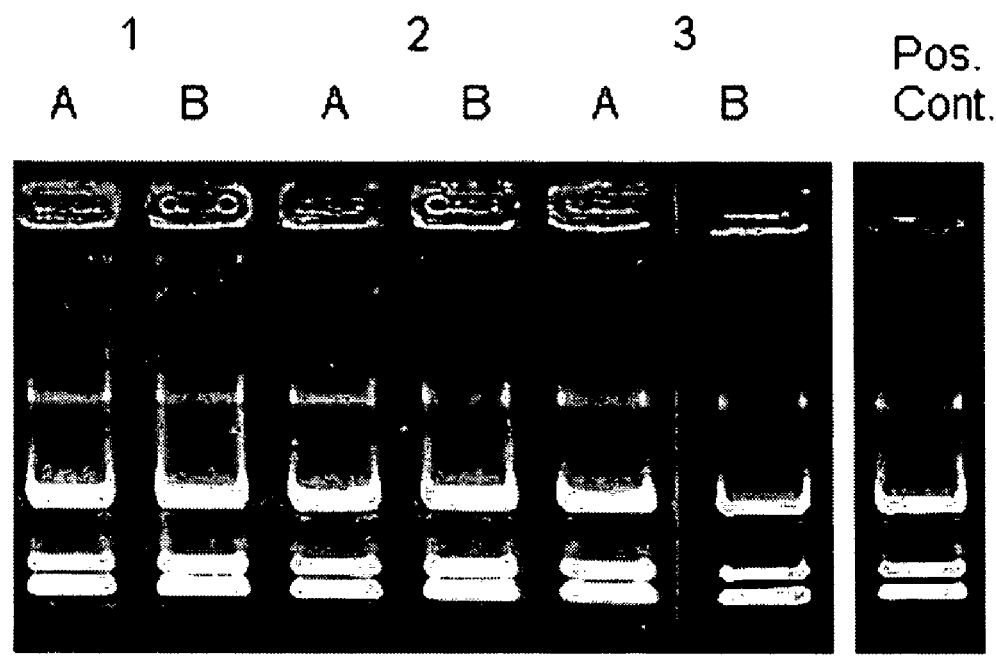

FIGS. 17 and 18 show amplification products obtained by multiplex PCR of *Salmonella* spp. inoculated on meat trimmings incubated with a standard method (FIG. 17), or an embodiment of the inventive 'dry' method (FIG. 18), for 7 h. Numbers 1, 2, 3 were inoculation levels at $1.6\times10^1$, $0.24\times10^1$, $0.042\times10^1$ CFU/g of meat, respectively. A and B were duplicate samples.

Figure 19:
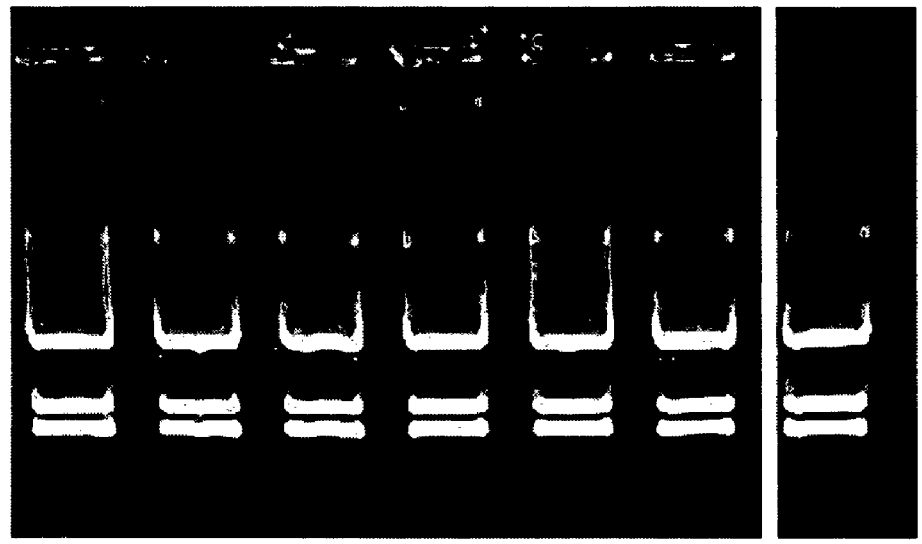
Figure 20:
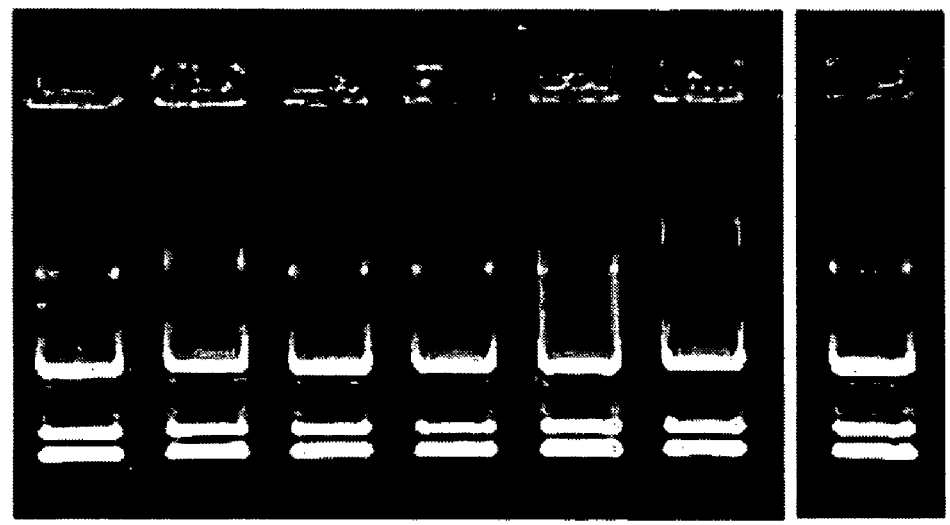

FIGS. 19 and 20 show amplification products obtained by multiplex PCR of *Salmonella* spp. inoculated on meat trimmings incubated with a standard method (FIG. 19), or an embodiment of the inventive 'dry' method (FIG. 20), for 8 h. Numbers 1, 2, 3 were inoculation levels at $1.6\times10^1$, $0.24\times10^1$, $0.042\times10^1$ CFU/g of meat, respectively. A and B were duplicate samples.

Figure 21:
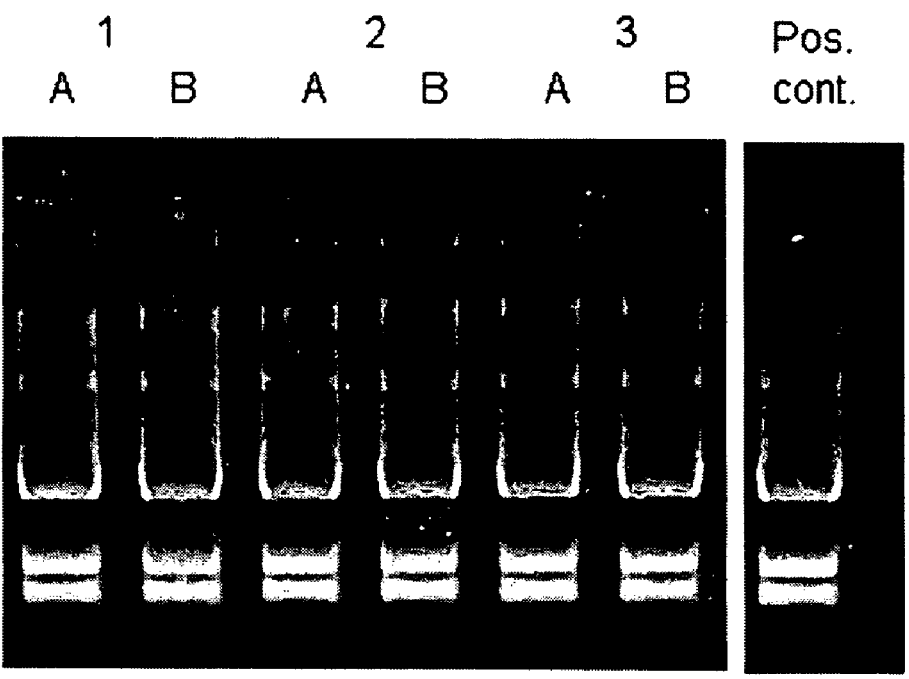
Figure 22:
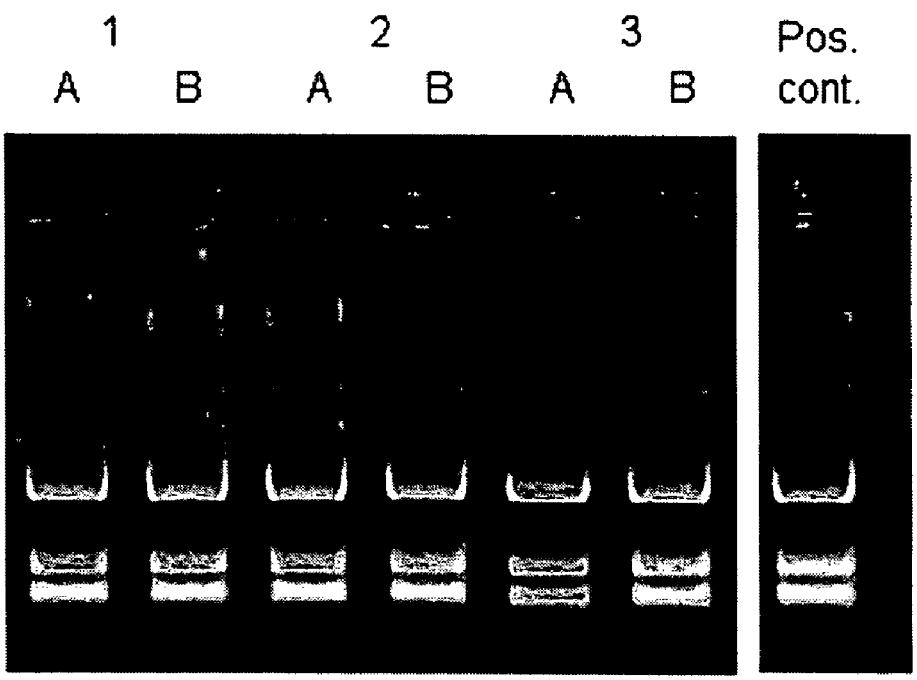

FIGS. 21 and 22 show amplification products obtained by multiplex PCR of *Salmonella* spp. inoculated on meat trimmings incubated with a standard method (FIG. 21), or an embodiment of the inventive 'dry' method (FIG. 22), for 24 h. Numbers 1, 2, 3 were inoculation levels at $1.6\times10^1$, $0.24\times10^1$, $0.042\times10^1$ CFU/g of meat, respectively. A and B were duplicate samples.

DETAILED DESCRIPTION OF THE INVENTION

Prior to the present invention, low-dilution enrichment, transit incubation methods were not known or appreciated in the relevant art. Prior art methods, as summarized herein, under the "Background" section, are based on 1:10 (wt./vol.) dilutions of the sample.

In various aspects, the present invention provides novel methods for remote testing of one or more pathogens or other microbes in food, water, wastewater, sludge, pharmaceutical, industrial samples, and the like. In particular aspects, a dry-enrichment or a semi-dry-enrichment process allows for incubation, during transit to a remote testing location, of the food samples either without (e.g., liquid samples) the addition of enrichment media, or with (e.g., solid or semi-solid samples) addition of only relatively small quantities of media and/or supplements, for testing at the remote location of contaminating pathogens or other microbes.

The present novel embodiments provide accurate, cost effective, and timely sampling and testing methods under circumstances where shipping of the sample to a remote testing location is required or desirable. The present invention, in various aspects, allows, inter alia, for: (i) savings in the cost of enrichment media/buffers; (ii) the ability to ship the samples economically (with up to 90% less weight), and with far less chances of spills (e.g., because of 90% less liquids in enriched samples), in specially designed dry/semi-dry shipping incubators, to remote/distant laboratories; (iii) increased sensitivity in the detection of the target organisms, due to smaller dilution factor; and (iv) the ability to form centralized laboratories (that may be remote from the sampling sites) that use the enrichment/incubation-in shipping concept to provide testing services to distant clients with the ability to report as fast as a local laboratory, and at similar or reduced costs relative to local laboratories.

According to the present invention, the samples are incubated immediately at the desired incubation temperature, and/or are incubated in transit by shipping the samples in a temperature-controlled shipping container or incubator allowing for incubation at appropriate temperatures within optimal ranges depending on the pathogen's optimal growth range, and/or optimal competitive growth range.

According to the present invention, for many types of foods, the food itself can be incubated with no addition of inhibitory or supplementary substances. For example, with foods or environmental samples that are in liquid form (e.g., fruit juices and the like), the samples are enriched directly, with or without a concentration step, with or without the addition of supplementary nutrients, inhibitors, or indicators.

In other aspects, with dry and semi-dry foods, the water and/or nutrient activity is adjusted to allow for the growth of the target organism. Addition of supplements depends on the target organism and the nature of the samples which are to be tested. Inventive supplements include water, sugars, proteins, minerals, organics, vitamins and cofactors, antibiotics, dyes, indicators, etc.

The protocols as described allow for the enrichment of pathogens, or target organisms with minimal increase in volume/weight of the samples. For samples that are to be shipped out, the shipping time can be used to enrich the sample without substantial increase in the weight and volume of the product, also minimizing the probability of spillage and/or cross-contamination. The sensitivity of the method is increased due to the elimination of dilution factor; the sample size has not increased substantially in terms of its volume or weight.

Samples testable according to the present invention include, but are not limited to beef, pork, sheep, bison, deer, elk, poultry (e.g., chicken and turkey) and fish, produce, juices, dairy products, dry goods (cereals, etc), and all manners of raw and processed foods, environmental samples (water, wastewater, soil, surface samples, samples taken by impingers and filtration, etc), pharmaceuticals, and other types of samples that are to be analyzed using enrichment-detection protocols.

DEFINITIONS

"Carcass" refers to the body of the livestock after harvest, de-hiding (or, as the case may be, de-feathering, de-skinning, de-scaling), and evisceration. Preferred embodiments relate to beef carcasses, but the present invention encompasses carcasses of pigs, sheep, deer, bison, elk, poultry (e.g., turkey, chicken) and other animals (e.g., fish) that are killed and processed into products that may contain pathogens and/or other microbes of interest.

Carcass "splitting" refers to splitting of the carcass into portions, including into two half-carcasses or half-carcass portions. In preferred embodiments, splitting refers to splitting into two half-carcass portions.

"Fabrication" refers to the process of cutting-up half-carcass into marketable cuts (e.g., primals, sub-primals, trim).

"Trim" refers to small pieces of meat and fat which are excised during the fabrication process in order to produce primal and subprimal pieces and marketable cuts.

"Trim testing" refers to the process of testing trim, or raw materials which are to be used for ground meat production for microbial/pathogen content.

A "combo" or "combo-bin" refers to the trim packaging unit. Alternatively raw materials to be tested can be packaged into boxes, bags or other appropriate containers, which can be placed, for example, on pallets.

A "Lot-unit" or "five-combo-lot unit" refers to a composite unit, comprised of five combos (combo-bins). In prior art sampling plans, the Lot-unit represents raw the material (composite trim) upon which sampling, testing and acceptance or rejection is based.

A prior art "Bin-sample" refers to a sample (typically about 75 g), comprised of 1-12 randomly-selected pieces from a single combo-bin. Typically, in prior art sampling plans, the standard manner of collection is to randomly pick five pieces as a comb-bin is being filled.

A prior art "Lot-unit sample" refers to a 375 g composite sample, comprised of seventy-five (75) gram samples from each combo-bin of the Lot-unit. In a variation of the typical prior art protocol, the random piece samples from each combo-bin (the Bin-samples) are subjected to grinding, then composite Lot-samples are made from the respective ground Bin-samples.

"Sampling" or "obtaining samples" refers to obtaining, in a form suitable for pathogen/microbe testing purposes, a sample of the pathogens and/or other microbes of interest present on or within various samples. Samples testable according to the present invention include, but are not limited to beef, pork, sheep, bison, deer, elk, poultry (e.g., chicken and turkey) and fish, produce, juices, dairy products, dry goods (cereals, etc), and all manners of raw and processed foods, environmental samples (water, wastewater, soil, surface samples, samples taken by impingers and filtration, etc), pharmaceuticals, and other types of samples that are to be analyzed using enrichment-detection protocols. Samples, include environmental samples, water, wastewater, samples taken by impingers and filtration, botanical liquid, industrial liquids, pharmaceutical liquids, and other liquid samples analyzed using enrichment-detection protocols.

For meat products, a sample may correspond to the surface of one or more test locations of the carcass or sub-carcass portion. Any sampling method is encompassed, provided that it is suitable to acquire (or include), at least to some extent, the surface pathogens/microbes. Preferably, the sampling method is by excision, or by blotting, swabbing, sponging, and the like (see under "Samples and Sample Locations, herein below).

PREFERRED EMBODIMENTS

Aspects of the present invention provide a method for remote detection of a pathogen or other microbe in a sample comprising: obtaining a test sample at a first location, the sample being solid or semi-solid; diluting, at the first location, the sample with enrichment medium at a ratio of about 1:2.0 (wt./vol.) or greater; incubating the diluted sample at an optimal temperature in an incubator during transit of the diluted sample to a second location that is a remote test location; and determining, at the remote test location, by assaying the diluted incubated test sample, or a portion thereof, with an assay suitable to detect the pathogen or other microbe, whether the sample is contaminated.

Preferably, the sample is selected from the group consisting of beef, pork, sheep, bison, deer, elk, poultry, fish, produce, dairy products, dry goods, raw and processed foods, environmental samples, soil, surface samples, samples taken by impingers and filtration, etc), pharmaceuticals, and samples analyzed using enrichment-detection protocols.

Preferably, diluting is at a ratio of 1:1 (wt./vol.) or greater. More preferably, diluting is at a ratio of 1:0.5 (wt./vol.) or greater. Alternatively, diluting is at a ratio of 1:0.3 (wt./vol.) or greater, or at a ratio of 1:01 (wt./vol.) or greater (i.e., non-diluted).

Preferably, the optimal temperature is within, or substantially within, the optimal growth temperature range of the pathogen or other microbe in the particular enrichment medium. Preferably, the optimal temperature is within, or substantially within, a temperature range that affords an optimal competitive growth advantage, relative to other microbes present in the sample. Preferably, the optimal temperature range is from about 25 to 45° C. Preferably, the optimal competitive growth temperature range is from about 30 to about 45° C.

Preferably, the assay suitable for detection of pathogenic or microbial contamination is selected from the assay group consisting of immunoassays, nucleic acid amplification-based assays, PCR-based assays, nucleic acid hybridization-based assays, bio-sensor assays, immunostaining-microscopy-based assays, nucleic acid-array-based assays, DNA chip-based assays, bacteriophage-detection-based assays, classical microbiology-based assays, and chemical or biochemical assays based on the detection of compounds associated with particular target organisms or groups of target organisms, and combinations thereof.

Preferably, the microbe or pathogen is selected from the group consisting of *Escherichia coli* O157:H7 (*E. coli* O157:H7), enterohemorrhagic *Escherichia coli* (EHEC), enterotoxigenic *Escherichia coli* (ETEC), enteroinvasive *Escherichia coli* (EIEC), enterpathogenic *Escherichia coli* (EPEC), *Salmonella, Listeria, Yersinis, Campylobacter, Clostridial species, Staphylococcus* spp.; frank and opportunistic bacterial, fungal, viral, parsitic pathogens; indicator organisms including heterotrophes, generic *E. coli*, total and fecal coliforms and enterococcus; spoilage organisms including *Pseudomonas*;

indicator molecules including glial fibillary acid protein (GFAP), transmissable spongiform encephalopathy (TSE) agents (prions), including bovine spongiform encephalopathy (BSE) agents, scrapie, chronic wasting disease; and combinations thereof.

Preferably, the pathogen or microbe is *Escerichia coli* O157:H7 (*E. coli* O157:H7).

Preferably, obtaining a sample is obtaining a sample from at least one test location of a carcass or of a split-portion thereof, wherein the test sample is obtained, in the slaughter production process, prior to or during initial chilling of the respective carcass or split-portion thereof. Preferably, the sample is a composite-Lot sample, corresponding to a combination of samples from a plurality of carcasses with a carcass Lot, and wherein the carcass is selected from the carcass group consisting of cattle, sheep, pigs, bison, elk, deer, chicken, turkey, fish and combinations thereof.

In alternative embodiments, supplements are added to the sample, prior to shipping of the sample to the remote testing location. Preferably, supplements are selected from the group consisting of water, sugars, proteins, minerals, organics, vitamins and cofactors, antibiotics, dyes, indicators. Such supplements are well known to those of ordinary skill in the relevant art, and include art-recognized micro-(e.g., Zn, Fe and Mn) and macro nutrients (e.g., Na, P, K, Ca, and magnesium and sulfur) (see, e.g., U.S. Pat. No. 5,582,627, incorporated by reference herein in its entirety), and/or carbon skeleton sources or other compounds, including but not limited to: sugar-mannose, lactose, dextrose, arythrose, fructose, fucose, galactose, glucose, gulose, maltose, polysaccharide, raffinose, ribose, ribulose, rutinose, saccharose, stachyose, trehalose, xylose, xylulose, adonose, amylose, arabinose, fructose phosphate, fucose-p, galactose-p, glucose-p, lactose-p, maltose-p, mannose-p, ribose-p, ribulose-p, xylose-p, xylulose-p, deoxyribose, corn steep liquor, whey, corn sugar, corn syrup, maple syrup, grape sugar, grape syrup, beet sugar, sorghum molasses, cane molasses, calcium lignosulfonate; sugar alcohol—adonitol, galactitol, glucitol, maltitol, mannitol, mannitol-p, ribitol, sorbitol, sorbitol-p, xylitol; organic acids—glucuronic acid, a-ketoglutaric acid, galactonic acid, glucaric acid, gluconic acid, pyruvic acid, polygalacturonic acid, saccharic acid, citric acid, succinic acid, malic acid, oxaloacetic acid, aspartic acid, phosphoglyceric acid, fulvic acid, ulmic acid, humic acid; nucleotides and bases—adenosine, adenosine-p, adenosine-p-glucose, uridine, uridine-p, uridine-p-glucose, thymine, thymine-p, cytosine, cytosine-p, guanosine, guanosine-p, guanosine-p-glucose, guanine, guanine-p, NADPH, NADH, FMN, FADH; Buffers—phosphate buffer, acetate buffer, AMP buffer, calcium tartrate, glycine buffer, phosphate citrate buffer, and tris buffer; and combinations thereof, are also contemplated (Id).

Optional addition of complexing agents, including but not limited to Citric acid; Ca, K, Na and ammonium lignosulfonates, fulvic acid, ulmic acid, humic acid, Katy-J, EDTA, EDDA, EDDHA, HEDTA, CDTA, PTPA, NTA and combination thereof, are also contemplated.

In alternate preferred embodiments, the invention provides a method for remote detection of a pathogen or other microbe in a liquid sample comprising: obtaining a liquid sample at a first location; incubating the sample at an optimal temperature in an incubator during transit of the diluted sample to a second location that is a remote test location; and determining, at the remote test location, by assaying the diluted incubated test sample, or a portion thereof, with an assay suitable to detect the pathogen or other microbe, whether the sample is contaminated.

Preferably, the optimal temperature is within, or substantially within, the optimal growth temperature range of the pathogen or other microbe in the particular enrichment medium. Preferably, the optimal temperature is within, or substantially within, a temperature range that affords an optimal competitive growth advantage, relative to other microbes present in the sample. Preferably, the optimal temperature range is from about 25 to about 45° C. Preferably, the optimal competitive temperature range is from about 30 to about 45° C.

Preferably, detection of pathogenic or microbial contamination is with an assay selected from the assay group consisting of immunoassays, nucleic acid amplification-based assays, PCR-based assays, nucleic acid hybridization-based assays, bio-sensor assays, immunostaining-microscopy-based assays, nucleic acid-array-based assays, DNA chip-based assays, bacteriophage-detection-based assays, classical microbiology-based assays, and chemical or biochemical assays based on the detection of compounds associated with particular target organisms or groups of target organisms, and combinations thereof.

Preferably, the microbe or pathogen is selected from the group consisting of *Escherichia coli* O157:H7 (*E. coli* O157:H7), enterohemorrhagic *Escerichia coli* (EHEC), enterotoxigenic *Escerichia coli* (ETEC), enteroinvasive *Escherichia coil* (EIEC), enteropathogenic *Escherichia coli* (EPEC), *Salmonella, Listeria, Yersinis, Campylobacter, Clostridial* species, *Staphylococcus* spp.; frank and opportunistic bacterial, fungal, viral, parsitic pathogens; indicator organisms including heterotrophes, generic *E. coli*, total and fecal coliforms and *enterococcus*; spoilage organisms including *Pseudomonas*; indicator molecules including glial fibillary acid protein (GFAP), transmissable spongiform encephalopathy (TSE) agents (prions), including bovine spongiform encephalopathy (BSE) agents, scrapie, chronic wasting disease; and combinations thereof.

Preferably, the pathogen or microbe is *Escherichia coli* O157:H7 (*E. coli* O157:H7).

Preferably, the liquid sample is selected from the group consisting of fruit juice, vegetable juice, milk and dairy products, raw and processed liquid foods, environmental samples, water, wastewater, samples taken by impingers and filtration, pharmaceuticals, and other samples analyzed using enrichment-detection protocols.

Alternatively, the methods comprise addition to the sample, prior to transit of the sample to the second location, of a supplement selected from the group consisting of water, sugars, proteins, minerals, organics, vitamins and cofactors, antibiotics, dyes, indicators, buffers and combinations thereof. Exemplary supplements are described elsewhere herein.

Yet further alternate embodiments provide a method for remote detection of a pathogen or other microbe in a solid sample, semi-solid sample or liquid sample comprising: obtaining a test sample at a first location, the sample being solid, semi-solid or liquid; diluting, at the first location, the sample with enrichment medium at a range of ratio of about 1:0.1 to 1:2 (wt./vol.), or not diluting the sample; incubating the enriched sample at an optimal temperature in an incubator for testing in a second location that is an in-house or local lab; and determining, at the in-house or local lab, by assaying the diluted incubated test sample, or a portion thereof, with an assay suitable to detect the pathogen or other microbe, whether the sample is contaminated.

Preferably, the methods further comprise addition to the sample, prior to or during incubation, of a supplement selected from the group consisting of water, sugars, proteins, minerals, organics, vitamins and cofactors, antibiotics, dyes, indicators, buffers, agents to adjust the pH, water activity, nutritional contents, selective pressure to optimize the growth conditions for the target organism, and combinations thereof.

Incubators

Preferred embodiments of the present invention comprise use of an incubator for holding the sample or diluted sample at an optimal temperature, or within an optimal temperature range, during shipment of the sample to the remote testing location. Suitable incubators are known in the art. In a preferred embodiment the incubator comprises an enclosure into which bottles containing sample and enrichment medium/buffer can be placed. Preferably the enclosure is an insulated container with a removable lid. Preferably, a temperature sensor activates 'on demand' power to a heating (and/or cooling) element. Preferably, the power supply is a typical 12 v type, able to work in a vehicle (e.g., off the cigarette lighter, or similar connection). In particular embodiments, a fan circulates air around the heating (and/or cooling) element. In preferred embodiments the power source is through a cigarette lighter-type connection within a vehicle. Preferably, the sample bottles are designed to be leak proof.

Samples to be Tested by the Inventive Methods

Samples testable according to the present invention include, but are not limited to beef, pork, sheep, bison, deer, elk, poultry (e.g., chicken and turkey) and fish, produce, juices, dairy products, dry goods (cereals, etc), and all manners of raw and processed foods, environmental samples (water, wastewater, soil, surface samples, samples taken by impingers and filteration, etc), pharmaceuticals, and other types of samples that are to be analyzed using enrichment-detection protocols.

Prior Art Trim Testing Methods in the Slaughter Industry

Prior art pathogen-testing plans are actually either trim-testing plans, final product testing plans, or both, involving random and incomplete sampling at the 'packing-Lot' level; that is, testing of trim samples near the end of the production chain (as they enter the bins or after binning, or testing of the ground products by taking samples at given time intervals. A typical trim-testing plan involves analysis of 'five-combo-lot' units, and comprises analysis of a single composite-Lot sample of about 375 g, prepared by combining five combo-bin samples (about 75 g each), in each case corresponding to one to five randomly-selected pieces from each combo-bin, such that, on average 5-25 pieces representing the five combo-bins are in the composite sample. The combo-bin is comprised of pieces of a plurality of carcasses, and thus the test results under these prior art systems reflect random and incomplete sampling; that is, only a small fraction of the carcasses are represented in the test results, particularly where, as is true of many such plans, only a sub-fraction of the composite-Lot sample is used for the pathogen-testing assay (e.g., when large pieces of trim are collected). For example, for ground beef production, final product testing comprises taking ground beef samples at given time intervals (e.g., every 10-30 minutes) and compositing a number of samples into one composite sample.

Generally, one of several methods of analysis has been used for pathogen detection after sampling at the packing-Lot level: (1) Immunochemical based detection (e.g., ELISA based immunoassays) following enrichment (e.g., for *E. coli* O157:H7); (2) Nucleic acid-based (e.g., DNA-based, such as PCR-analysis) detection methods following enrichment (e.g., for *E. coli* O157:H7), wherein an appropriate medium is inoculated with a composite-Lot sample; and (3) target organisms can be detected by enrichment, followed by immunomagnetic separation followed by plating, immunochemical or DNA based detection. Typically, the levels of sensitivity of most of these methods are set at about 1 colony forming unit (cfu)/25 g of sample.

Typically, to allow time for trim testing results to be obtained, such sampling plans require additional (in addition to initial chilling of the split-carcasses, and the time taken during the processing of the carcasses (fabrication)) 'holding' of the trim prior to use. Such holding of the trim will typically add 12 to 24 hrs of extra refrigeration storage time/capacity, and uses up about a day of the product shelf-life.

Trim Testing Methods in the Context of the Present Invention

According to preferred aspects of the present invention, carcasses (e.g., beef, sheep, pigs, deer, elk, bison, poultry, and fish) typically spend up to 24 hours in chilled storage prior to being cut up into, or generating, trim (prior to fabrication), and this is sufficient time to run an adequate detection assay (e.g., presence/absence assays) for microbes or other pathogens. Furthermore, carcass-Lots are identifiable, and carcasses are typically tagged with unique identifiers, and thus, according to the present invention, where a timely and statistically-significant positive result (contaminated carcass) is obtained, the respective contaminated carcass-Lot is precluded from entering the fabrication/production chain. Therefore, cross-contamination is reduced or eliminated, where carcasses carrying contamination are removed from the process stream prior to being cut into, or generating, trim (e.g., the possibility of transferring any contamination to equipment such as knives and conveyor belts is reduced or eliminated).

In a preferred aspect, the inventive method comprises splitting of a carcass-Lot to produce a split-carcass-Lot (Lot of split-portions), and obtaining at least one surface test sample from at least one preferred sample location of one or both split-portions, immediately prior to chilling of the split-portions. In a particularly preferred embodiment, at least three distinct surface samples are taken from each half-carcass. The test samples are combined to form a composite-Lot test sample, and the composite-Lot test sample, or a portion thereof is used for determining whether contamination is present by using an assay suitable to detect the microbe or pathogen of interest. Preferably, a carcass-Lot is a group of 50-100 carcasses. Preferably, at least one half of each carcass is surface-sampled (e.g., by excision, blotting, swabbing or sponging). Preferably, testing is of composite-Lot samples comprising at least 25, at least 50, at least 100, at least 150, at least 200, or at least 300 surface samples (e.g., blotting, swabbing or sponging, or thinly excised sample slices). Preferably, three to four carcass sampling stations (locations) are established. Preferably, the sampling stations correspond to carcass sites that are most likely, according to the present invention, to be contaminated, based on factors regarding the locations and incident rates of a given pathogen such as *E. coli* O157:H7. Preferably, the test locations are selected in a random or repeated (rotational) order from the group consisting of rump, brisket, back and flank, and combinations thereof. Preferably, from rump, brisket and/or flank.

Type of Pathogens/Microbes to be Detected

In preferred embodiments, the present inventive methods encompass the detection of *Escherichia coli* O157:H7 (*E. coli* O157:H7), enterohemorrhagic *Escherichia coli* (EHEC), enterotoxigenic *Escherichia coli* (ETEC), enteroinvasive *Escherichia coli* (EIEC), enterpathogenic *Escherichia coli* (EPEC), *Salmonella, Listeria, Yersinis, Campylobacter, Clostridial species, Staphylococcus spp.* Additionally, other pathogens and pathogenic agents are encompassed within the present invention, including, but not limited to other frank and opportunistic bacterial, fungal, viral, parsitic pathogens; indicator organisms (total heterotrophes, generic *E. coli*, total and fecal coliforms, enterococcus, etc); and spoilage organisms (*Pseudomonas*, etc), and indicator molecules such as glial fibillary acid protein (GFAP), transmissable spongiform encephalopathy (TSE) agents (prions) (e.g., bovine spongiform encephalopathy (BSE) agents, scrapie (sheep), chronic wasting disease (e.g., deer, Elk).

Preferably, the detected microbe is: a pathogen including, but not limited to, *Escherichia coli* O157:H7 (*E. coli* O157:H7), *Listeria, Salmonella*, EHEC, *Campylobacter, Staphylococcus*, pathogenic Clostridial species, and other frank, or opportunistic pathogens; a spoilage organism including, but not limited to, clostridial and pseudomonas species; or an indicator organism including, but not limited to, generic *E. coli*, fecal coliforms, total coliforms, etc. More preferably, the pathogen is *Escherichia coli* O157:H7 (*E. coli* O157:H7).

Detection Assays

Preferably, the detection assay is selected from the assay group consisting of immunoassays, nucleic acid amplification-based (e.g., PCR-based assays), nucleic acid hybridization-based assays, bio-sensor assays, immunostaining-microscopy based assays, nucleic acid-array-based (e.g., DNA chip-based) assays, bacteriophage detection based assays, classical microbiology based assays, and chemical/biochemical assays based on the detection of compounds associated with particular groups of target organisms, and combinations thereof. Such assays are well known in the relevant art, and a few exemplary assays are as follows:

Reveal® test kits are available from Neogen Corporation, Lansing, Mich., and comprise an ELISA test that combines an immunoassay with chromatography in a lateral flow device (Reveal test kits are available for *E coli* O157:H7, *Salmonella, Listeria* spp. and *Listeria monocytozenes*);

VIP(D test kits are available from BioControl, Bellevue, Wash., and comprise an ELISA test that is expressed as a lateral flow antibody-chromogen immunoprecipitate assay (VIP® test kits are available for EHEC, *Salmonella, Listeria* spp. and *Listeria monocytogenes*);

BAX® Qualicon test kits are available from DuPont, Wilmington, Del., wherein, using the BAX® system, samples are enriched and then lysed to release DNA, which is amplified using PCR techniques, and detected using a fluorescent signal (BAX® test kits are available for *E. coli* O157:H&, *Salmonella. Listeria* spp. and *Listeria monocytogenes*, and *enterobacter sakazakii*); and TSE (e.g., in cattle sheep and deer) can be tested by testing nervous system tissue (e.g., brain stem) for the respective agents (PrP) using, for example, ELISA assays, such as the Enfer TSE test, manufactured by Enfer Scientific, Newbridge Ireland, and distributed by Abbott Laboratories (Abbott Park, Ill.; see Abbott Application Note by Klass et al, 2002, "A test for transmissible spongiform encephalopathy," incorporated herein by reference).

Carcass Samples and Sample Locations

Sampling, as practiced herein, refers to obtaining, in a form suitable for pathogen/microbe testing purposes, a sample of the pathogens and/or other microbes of interest present on the surface of one or more test locations of the carcass or sub-carcass portion. Any sampling method is encompassed, provided that it is suitable to extract (or include), at least to some extent, the surface pathogens/microbes. Preferably, the sampling method is by excision, or by blotting, swabbing, sponging, and the like. Preferably, in order to produce results which allow systematic comparisons with additional monitoring of microbial interventions along process line, samples are collected at the rump, brisket, or flank and combinations thereof (see Elder et al., *PNAS* 97:2999-3003, 2000; Correlation of enterohemorrhagic *Escherichia coli* O157 prevalence in feces, hides, and carcasses of beef cattle during processing).

Preferably, obtaining a test sample, or remedial test sample, comprises obtaining one or more surface samples from at least one test location of at least one split-portion, or remedial-split-portion of each carcass. Preferably, the test sample, or remedial test sample, is a surface sample (e.g., swabbed, blotted, sponged, or an excised surface tissue section) corresponding to, or having a surface area of at least 4, at least 6, at least 8, at least 10, at least 12, or at least 16 square inches. More preferably, the test sample, or remedial test sample, is a surface sample corresponding to, or having a dimension of about 16 square inches. Preferably, the test sample, or remedial test sample, comprises three, or at least three, such surface samples, each from a distinct location of the split-portion. Preferably, the test location, or remedial test location, is randomly or rotationally selected from the group consisting of sites most likely to harbor microbial pathogens (e.g., rump, brisket, back and flank, and combinations thereof).

In particularly preferred embodiments, a contaminated split-carcass-Lot is subjected to remedial reconditioning. Preferably, reconditioning comprises sanitizing/pasteurizing by hot-water or steam pasteurization, and/or by using an organic acid spray, (e.g., lactic-acid spray), etc.). Such methods are well known to those of ordinary skill in the relevant art.

The present invention will now be further illustrated by reference to the following EXAMPLES. However, it should be noted that these EXAMPLES, like the embodiments described above, are illustrative and are not to be construed as restricting the enabled scope of the invention in any way.

EXAMPLE I

Enrichment Methods Based on 1:0.5 Dilution Samples to Media Were Found to be Effective)

To compare the effectiveness of dry (1:0.5 meat to media) to standard (1:10) enrichment methods on the growth of *Escerichia coli* O157:H7 and *Salmonella* spp. on experimentally inoculated meat samples incubated for 6, 7, 8, and 24 h. *E. coli* and *Salmonella* spp. were detected with a multiplex polymerase chain reaction (PCR) technique.

Materials and Methods

Inoculum preparation. Colonies of *E. coli* O157:H7 and *Salmonella typhi* isolated from clinical samples were grown on MacConkey II agar (BD Diagnostic Systems, Sparks, Md.) and XLD (BD), respectively. Random colonies of *E. coli* O157 were confirmed with *E. coli* O157 Latex Test Kit (Oxoid, Hampshire, UK). Each pathogen were independently cultured in *E. coli* O157 Bax® System media (Dupont Qualicon by Oxoid Ltd., Hampshire, England) at 37° C. for 24 h. Serial dilutions of each inoculum were done separately in 0.1% peptone water (BD). Enumeration was done by plating 1 ml of each dilution on Petrifilm™ Aerobic Count Plates (3M™ Microbiology Products, St. Paul, Minn.). Plates were incubated at 37° C. for up to 48 h. Based on enumeration data, meat trim samples were inoculated with approximately $6.1 \times 10^2$, $9.1 \times 10^1$, and $0.9 \times 10^1$ CFU/ml of *E. coli* O157:H7, and $4.1 \times 10^2$, $6.2 \times 10^1$, and $1.0 \times 10^1$ CFU/ml of *S. typhi*.

Meat sample. Prepacked meat trim (beef stew) sample was purchased from a local grocery store in Seattle, Wash. For standard and dry enrichment methods, 25 g and 100 g of duplicate samples were placed in whirl-pack bags, respectively. Meat samples were inoculated with three concentrations of E. coli O157:H7 and S. typhi mentioned earlier at a rate of 1 ml of each pathogen per 25 g of meat sample. This approached resulted in concentrations of $2.4 \times 10^1$, $0.36 \times 10^1$, and $0.036 \times 10^1$ CFU/g of meat for E. coli O157:H7, and $1.67 \times 10^1$, $0.24 \times 10^1$, $0.042 \times 10^1$ CFU/g of meat for S. typhi. Samples were then subjected to a stomacher for 30 s. Standard and dry enrichment samples received 225 ml and 50 ml of pre-warmed (42° C.) E. coli O157 Bax® System media (Dupont), respectively. Samples were again stomached for 30 s. All enrichment bags were placed in an incubator shaker at 42° C. with household (ice) packs between bags. Ice packs were pre-warmed by placing them in a 42° C. incubator two days prior to the experiment.

At 6, 7, 8 and 24 h of incubation, 1 ml of broth of each enrichment bag was taken and placed in 1.5 ml centrifuge tubes. Samples were concentrated by centrifugation for 5 min at low speed. Supernatant was aspirated and pellet was resuspended in 1 ml phosphate buffer saline with 0.05% Tween (PBST).

Prior to E. coli O157:H7 detection by PCR method, an aliquot of sample suspension was concentrated with anti-E. coli O157 Dynabeads® (Dynal Biotech ASA, Oslo, Norway). All sample suspension with and without Dynabeads® were detected by PCR.

Background microflora of non-inoculated meat sample was analyzed. Ten grams of meat sample was placed in a stomacher bag and 90 ml of 0.1% peptone water was added to the bag. The meat was subjected to a stomacher for 30 s. Serial dilution was made in 0.1% peptone water and 1 ml was plated on Petrifilm™ Aerobic Count Plates (3M™). Plates were incubated at 37° C. for up to 48 h.

PCR. Multiplex PCR method was used for the detection of E. coli O157:H7 and Salmonella spp. A reaction mixture containing specific regions of the pathogens of interest was used as a positive control. Negative control was distilled water.

E. coli O157: Samples were subjected to a 55 μl mixture of lysis buffer containing $MgCl_2$ IGEPAL CA-630 detergent, primers, achromopeptidase and Tris buffer. The primer pairs amplified specific fragments of E. coli O157:H7 encoding for O157 antigen (rfb, 985 bp), intemin (eae, 309 bp), and shiga-like toxin 2 (six 2,255 bp) and 1 (stx 1,180 bp) genes. Pure Taq Ready-To-Go beads (Amersham Biosciences, Piscataway, N.J.) were used. Taq beads contained Taq polymerase, dNTPs, BSA, and detergent. The reaction conditions were 4° C. for 2 min, 95° C. for 2 min, 95° C. for 2 sec, 65° C. for 30 sec, 72° C. for 20 sec, 33 cycles of 95° C. for 10 sec, followed by 4° C. cooling period.

Salmonella spp.: Samples were subjected to a 55 μl mixture of lysis buffer containing $MgCl_2$ IGEPAL CA-630 detergent, primers, achromopeptidase and Tris buffer. The primer pairs amplified specific fragments of Salmonella spp. encoding for plasmid DNA (524 bp), Salmonella spp. fragment (300 bp), and chromosome (197 bp) genes. Pure Taq Ready-To-Go beads (Amersham Biosciences) were used. Taq beads contained Taq polymerase, dNTPs, BSA, and detergent. The reaction conditions were 4° C. for 2 min, 95° C. for 2 min, 95° C. for 2 sec, 65° C. for 30 sec, 72° C. for 20 sec, 33 cycles of 95° C. for 10 sec, followed by 4° C. cooling period.

Electrophoresis was performed on 2% (w/v) agarose gel (Fisher Scientific, Fair Lawn, N.J.), stained with ethidium bromide solution and viewed under a UV light source.

Results

Pre-packed meat trim had an average of 3.8 logs CFU/ml of aerobic plate counts. The four (rfb, eae, stx 1, and stx 2) target genes for E. coli O157 were detected by PCR methods with Dynabeads® (FIGS. 1 through 6) and without Dynabeads® (FIGS. 7 through 14) from samples incubated with dry and standard enrichment procedures for 6, 7, 8, and 24 h incubation. Likewise, the three (spvc, sal 2, and inva) target genes for Salmonella spp. were detected by PCR methods (FIGS. 14 through 22) from samples incubated with dry and standard enrichment procedures after 6, 7, 8, and 24 h incubation.

FIG. 1 shows amplification products obtained by multiplex PCR of E. coli O157:H7 inoculated on meat trimmings incubated with standard dilution method (1:10) for 6 h and concentrated by Dynabeads®. Numbers 1, 2, 3 were inoculation levels at $2.4 \times 10^1$, $0.36 \times 10^1$, and $0.036 \times 10^1$ CFU/g of meat, respectively. A and B were duplicate samples.

Figure 2:
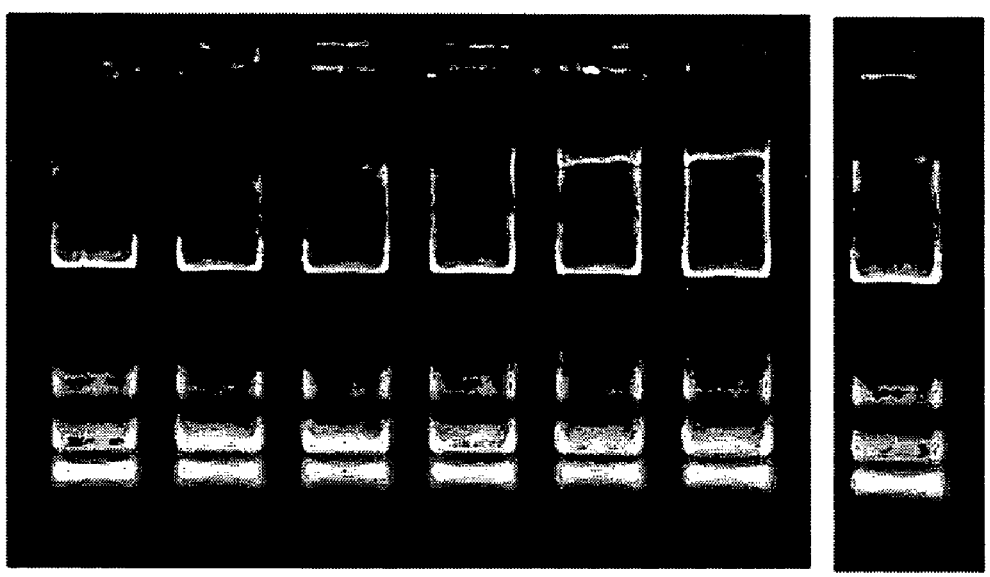

FIG. 2 shows amplification products obtained by multiplex PCR of E. coli O157:H7 inoculated on meat trimmings incubated with a representative dry method (1:0.5) for 6 h and concentrated by Dynabeads®. Numbers 1, 2, 3 were inoculation levels at $2.4 \times 10^1$, $0.36 \times 10^1$, and $0.036 \times 10^1$ CFU/g of meat, respectively. A and B were duplicate samples.

Figure 3:
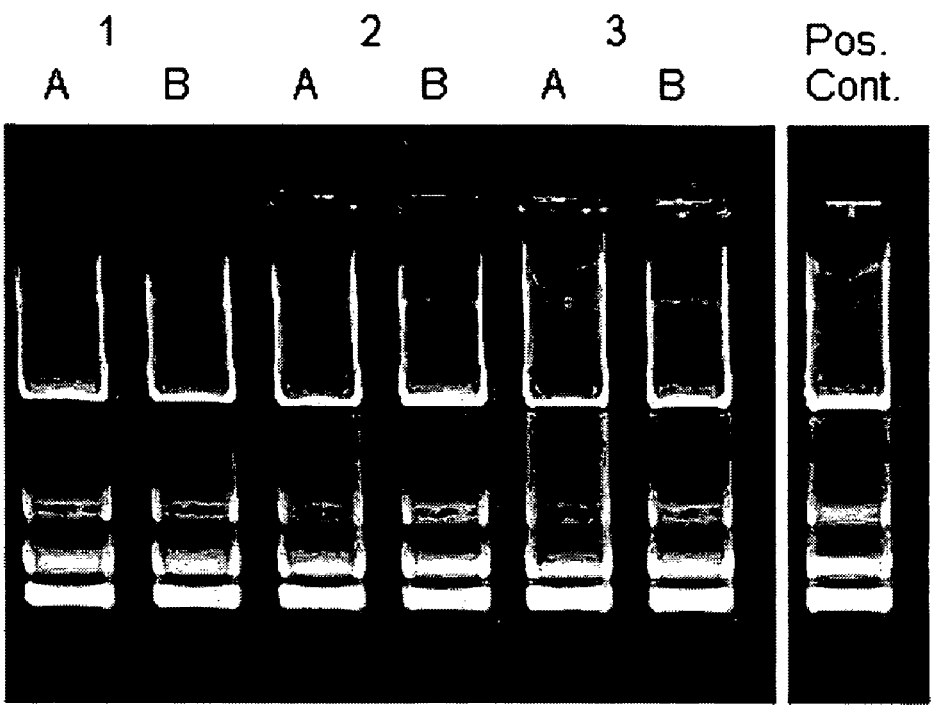

FIG. 3 shows amplification products obtained by multiplex PCR of E. coli O157:H7 inoculated on meat trimmings incubated with standard method (1:10) for 7 h and concentrated by Dynabeads®. Numbers 1, 2, 3 were inoculation levels at $2.4 \times 10^1$, $0.36 \times 10^1$, and $0.036 \times 10^1$ CFU/g of meat, respectively. A and B were duplicate samples.

Figure 4:
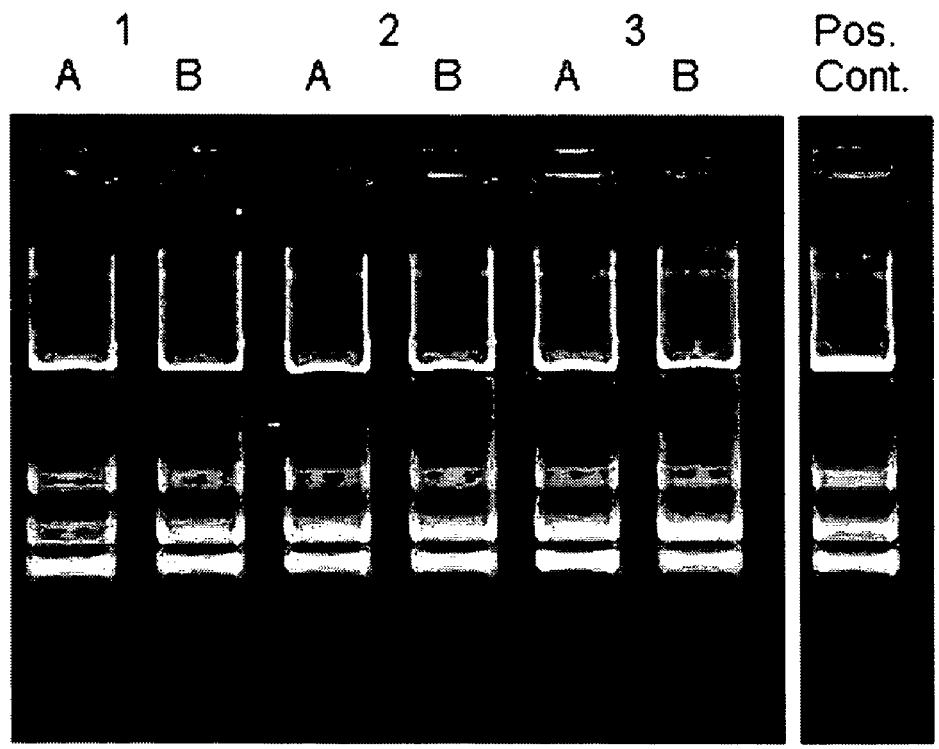

FIG. 4 show amplification products obtained by multiplex PCR of E. coli O157:H7 inoculated on meat trimmings incubated with dry method (1:0.5) for 7 h and concentrated by Dynabeads®. Numbers 1, 2, 3 were inoculation levels at $2.4 \times 10^1$, $0.36 \times 10^1$, and $0.036 \times 10^1$ CFU/g of meat, respectively. A and B were duplicate samples.

FIG. 5 shows amplification products obtained by multiplex PCR of E. coli O157:H7 inoculated on meat trimmings incubated with standard method (1:10) for 8 h and concentrated by Dynabeads®. Numbers 1, 2, 3 were inoculation levels at $2.4 \times 10^1$, $0.36 \times 10^1$, and $0.036 \times 10^1$ CFU/g of meat, respectively. A and B were duplicate samples.

FIG. 6 shows amplification products obtained by multiplex PCR of E. coli O157:H7 inoculated on meat trimmings incubated with dry method (1:0.5) for 8 h and concentrated by Dynabeads®. Numbers 1, 2, 3 were inoculation levels at $2.4 \times 10^1$, $0.36 \times 10^1$, and $0.036 \times 10^1$ CFU/g of meat, respectively. A and B were duplicate samples.

FIG. 7 shows amplification products obtained by multiplex PCR of E. coli O157:H7 inoculated on meat trimmings incubated with standard method (1:10) for 6 h. Numbers 1, 2, 3 were inoculation levels at $2.4 \times 10^1$, $0.36 \times 10^1$, and $0.036 \times 10^1$ CFU/g of meat, respectively. A and B were duplicate samples.

FIG. 8 shows amplification products obtained by multiplex PCR of E. coli O157:H7 inoculated on meat trimmings incubated with dry method (1:0.5) for 6 h. Numbers 1, 2, 3 were inoculation levels at $2.4 \times 10^1$, $0.36 \times 10^1$, and $0.036 \times 10^1$ CFU/g of meat, respectively. A and B were duplicate samples.

FIG. 9 shows amplification products obtained by multiplex PCR of E. coli O157:H7 inoculated on meat trimmings incubated with standard method (1:10) for 7 h. Numbers 1, 2, 3 were inoculation levels at $2.4 \times 10^1$, $0.36 \times 10^1$, and $0.036 \times 10^1$ CFU/g of meat, respectively. A and B were duplicate samples.

FIG. 10 mplification products obtained by multiplex PCR of E. coli O157:H7 inoculated on meat trimmings incubated with dry method (1:0.5) for 7 h. Numbers 1, 2, 3 were inoculation levels at $2.4 \times 10^1$, $0.36 \times 10^1$, and $0.036 \times 10^1$ CFU/g of meat, respectively. A and B were duplicate samples.

FIG. 11 shows amplification products obtained by multiplex PCR of E. coli O157:H7 inoculated on meat trimmings incubated with standard method (1:10) for 8 h. Numbers 1, 2, 3 were inoculation levels at $2.4\times10^1$, $0.36\times10^1$, and $0.036\times10^1$ CFU/g of meat, respectively. A and B were duplicate samples.

FIG. 12 shows amplification products obtained by multiplex PCR of E. coli O157:H7 inoculated on meat trimmings incubated with dry method (1:0.5) for 8 h. Numbers 1, 2, 3 were inoculation levels at $2.4\times10^1$, $0.36\times10^1$, and $0.036\times10^1$ CFU/g of meat, respectively. A and B were duplicate samples.

FIG. 13 shows amplification products obtained by multiplex PCR of E. coli O157:H7 inoculated on meat trimmings incubated with standard method (1:10) for 24 h. Numbers 1, 2, 3 were inoculation levels at $2.4\times10^1$, $0.36\times10^1$, and $0.036\times10^1$ CFU/g of meat, respectively. A and B were duplicate samples.

FIG. 14 shows amplification products obtained by multiplex PCR of E. coli O157:H7 inoculated on meat trimmings incubated with dry method (1:0.5) for 24 h. Numbers 1, 2, 3 were inoculation levels at $2.4\times10^1$, $0.36\times10^1$, and $0.036\times10^1$ CFU/g of meat, respectively. A and B were duplicate samples.

FIG. 15 shows amplification products obtained by multiplex PCR of Salmonella spp. inoculated on meat trimmings incubated with standard method (1:10) for 6 h. Numbers 1, 2, 3 were inoculation levels at $1.6\times10^1$, $0.24\times10^1$, $0.042\times10^1$ CFU/g of meat, respectively. A and B were duplicate samples.

FIG. 16 shows amplification products obtained by multiplex PCR of Salmonella spp. inoculated on meat trimmings incubated with dry method (1:0.5) for 6 h. Numbers 1, 2, 3 were inoculation levels at $1.6\times10^1$, $0.24\times10^1$, $0.042\times10^1$ CFU/g of meat, respectively. A and B were duplicate samples.

FIG. 17 shows amplification products obtained by multiplex PCR of Salmonella spp. inoculated on meat trimmings incubated with standard method (1:10) or 7 h. Numbers 1, 2, 3 were inoculation levels at $1.6\times10^1$, $0.24\times10^1$, $0.042\times10^1$ CFU/g of meat, respectively. A and B were duplicate samples.

FIG. 18 shows amplification products obtained by multiplex PCR of Salmonella spp. inoculated on meat trimmings incubated with dry method (1:0.5) for 7 h. Numbers 1, 2, 3 were inoculation levels at $1.6\times10^1$, $0.24\times10^1$, $0.042\times10^1$ CFU/g of meat, respectively. A and B were duplicate samples.

FIG. 19 shows amplification products obtained by multiplex PCR of Salmonella spp. inoculated on meat trimmings incubated with standard method (1:10) for 8 h. Numbers 1, 2, 3 were inoculation levels at $1.6\times10^1$, $0.24\times10^1$, $0.042\times10^1$ CFU/g of meat, respectively. A and B were duplicate samples.

FIG. 20 shows amplification products obtained by multiplex PCR of Salmonella spp. inoculated on meat trimmings incubated with dry method (1:0.5) for 8 h. Numbers 1, 2, 3 were inoculation levels at $1.6\times10^1$, $0.24\times10^1$, $0.042\times10^1$ CFU/g of meat, respectively. A and B were duplicate samples.

FIG. 21 shows amplification products obtained by multiplex PCR of Salmonella spp. inoculated on meat trimmings incubated with standard method (1:10) for 24 h. Numbers 1, 2, 3 were inoculation levels at $1.6\times10^1$, $0.24\times10^1$, $0.042\times10^1$ CFU/g of meat, respectively. A and B were duplicate samples.

FIG. 22 shows amplification products obtained by multiplex PCR of Salmonella spp. inoculated on meat trimmings incubated with dry method (1:0.5) for 24 h. Numbers 1, 2, 3 were inoculation levels at $1.6\times10^1$, $0.24\times10^1$, $0.042\times10^1$ CFU/g of meat, respectively. A and B were duplicate samples.

Collectively, the results show that enrichment of meat trimmings with the inventive 'dry' method (e.g., 1:0.5 wt./vol. dilution) gave results comparable to those obtained using standard (USDA) methods employing the art-recognized 1:10 dilution factor. This experiment showed that enrichment of meat trimming with 'dry' method (1:0.5 dilution) showed similar results to the standard FDA (1:10 dilution) method. This experiment also showed that the dry enrichment method on samples inoculated with the highest ($0.021\times10^1$ CFU/g) dilution of bacteria was able to produce sufficient signals as shown in the PCR results.

EXAMPLE II

Costs comparisons of the inventive methods with those of the prior art are as follows:

TSB medium comparison:
  TSB 1 lb (453.59 g)=>$25-27 (depending on quantity ordered);
  Working dilution: 30 g/L;
  From 453.59 g, make ±15.11 L;
  Price per Liter=±$1.65 to $1.78;
  Prior art price per sample (225 ml)=(225/1000) *1.65=±$0.37 to $0.40; and
  Inventive method price per sample (50 ml)=(50/1000) *1.65=±$0.082 to 0.089.

TSB medium comparison:
  E. coli O157 Bax® System media (Dupont Qualicon by Oxoid Ltd., Hampshire, England);
  2.5 Kg (2500 g)=<about $300.00;
  Working dilution: 36.6 g/L;
  From 2,500 g, make ±68.3 L;
  Price per liter=±$4.39;
  Prior art price per sample (225 ml)=(225/1000)* 4.39 =$0.98; and
  Inventive method price per sample (50 ml)=(50/1000)* 4.39=±$0.21.

The invention claimed is:

1. A method for detection of a particular pathogen or other microbe, comprising:
   obtaining a test sample at a first location, the sample being solid or semi-solid;
   diluting, at the first location, the sample with liquid enrichment medium at a ratio of sample to diluent of between about 1:0.1 to about 1:2 (wt./vol.), or lesser dilution;
   incubating the diluted sample at an optimal temperature for the particular pathogen or other microbe to be detected in an incubator during transit of the diluted sample to a second remote location that is not the site of sample collection; and
   determining, at the remote test location, by assaying the diluted incubated test sample, or a portion thereof, with an assay suitable to detect the particular pathogen or other microbe, whether the sample is contaminated with the particular pathogen or other microbe.

2. The method of claim 1, wherein diluting is at a ratio of 1:2 (wt./vol.) or lesser dilution.

3. The method of claim 1, wherein diluting is at a ratio of 1:0.5 (wt./vol.) or lesser dilution.

4. The method of claim 1, wherein diluting is at a ratio of 1:0.1 (wt./vol.) or lesser dilution.

5. The method of claim 1, wherein the optimal temperature is within the optimal growth temperature range of the particular pathogen or other microbe in the liquid enrichment medium.

6. The method of claim 5, wherein the optimal temperature range is from about 25 to about 45° C.

7. The method of claim 1, wherein the assay suitable for detection of pathogenic or microbial contamination is selected from the assay group consisting of immunoassays, nucleic acid amplification-based assays, PCR-based assays, nucleic acid hybridization-based assays, bio-sensor assays, immunostaining-microscopy-based assays, nucleic acid-array-based assays, DNA chip-based assays, bacteriophagedetection-based assays, classical microbiology-based assays, and chemical or biochemical assays based on the detection of compounds associated with particular target organisms or groups of target organisms, and combinations thereof.

8. The method of claim 1, wherein the microbe or pathogen is selected from the group consisting of *Escherichia coli* O157:H7 (*E. coli* O157:H7), enterohemorrhagic *Escherichia coli* (EHEC), enterotoxigenic *Escherichia coli* (ETEC), enteroinvasive *Escherichia coli* (EIEC), enterpathogenic *Escherichia coli* (EPEC), *Salmonella, Listeria, Yersinis, Campylobacter, Clostridial* species, *Staphylococcus* spp.; frank and opportunistic bacterial, fungal, viral, parasitic pathogens; indicator organisms including heterotrophes, generic *E. coli*, total and fecal coliforms and enterococcus; spoilage organisms including *Pseudomonas*; and combinations thereof.

9. The method of claim 8, wherein the pathogen or microbe is selected from the group consisting of *Escherichia coli* O157:H7 (*E. coli* O157:H7, or H negative), *Salmonella, Listeria*, EHEC, and *Campylobacter*.

10. The method of claim 1, wherein obtaining a sample is obtaining a standard Lot-unit sample.

11. The method of claim 1, wherein the sample is a composite-Lot sample, corresponding to a combination of samples selected from the group consisting of samples or subsamples taken from sublots/lots of raw or processed samples, environmental samples, industrial samples, pharmaceutical samples, water samples, wastewater samples, biosolid samples, air samples, samples taken by spore traps, settled dust, impingers, or filtration, and combinations thereof.

12. A method for detection of a particular pathogen or other microbe, comprising:
obtaining a liquid sample at a first location;
diluting, at the first location, the sample with liquid enrichment medium at a ratio of sample to diluent of between about 1:0.1 to about 1:2 (wt./vol.) or lesser dilution, or not diluting the sample;
incubating the sample at an optimal temperature for the particular pathogen or other microbe to be detected in an incubator during transit of the diluted sample to a second remote location that is not the site of sample collection; and
determining, at the remote test location, by assaying the diluted or undiluted incubated test sample, or a portion thereof, with an assay suitable to detect the particular pathogen or other microbe, whether the sample is contaminated with the particular pathogen or other microbe.

13. The method of claim 12, wherein the optimal temperature is within the optimal growth temperature range of the particular pathogen or other microbe in the liquid enrichment medium.

14. The method of claim 13, wherein the optimal temperature range is from about 25 to about 45° C.

15. The method of claim 12, wherein the assay suitable for detection of pathogenic or microbial contamination is selected from the assay group consisting of immunoassays, nucleic acid amplification-based assays, PCR-based assays, nucleic acid hybridization-based assays, bio-sensor assays, immunostaining-microscopy-based assays, nucleic acid-array-based assays, DNA chip-based assays, bacteriophage-detection-based assays, classical microbiology-based assays, and chemical or biochemical assays based on the detection of compounds associated with particular target organisms or groups of target organisms, and combinations thereof.

16. The method of claim 12, wherein the microbe or pathogen is selected from the group consisting of *Escherichia coli* O157:H7 (*E. coli* O157:H7), enterohemorrhagic *Escherichia coli* (EHEC), enterotoxigenic *Escherichia coli* (ETEC), enteroinvasive *Escherichia coli* (EIEC), enterpathogenic *Escherichia coli* (EPEC), *Salmonella, Listeria, Yersinis, Campylobacter, Clostridial* species, *Staphylococcus* spp.; frank and opportunistic bacterial, fungal, viral, parasitic pathogens; indicator organisms including heterotrophes, generic *E. coli*, total and fecal coliforms and enterococcus; spoilage organisms including *Pseudomonas*; and combinations thereof.

17. The method of claim 16, wherein the pathogen or microbe is selected from the group consisting of *Escherichia coli* O157:H7 (*E. coli* O157: or H negative), *Salmonella, Listeria*, EHEC, and *Campylobacter*.

18. The method of claim 1, where in the sample is selected from the group consisting of beef, pork, sheep, bison, deer, elk, poultry, fish, produce, dairy products, dry goods, raw and processed foods, environmental samples, soil, sludge, surface samples, samples taken by impingers and filtration, pharmaceuticals, and samples analyzed using enrichment-detection protocols.

19. The method of claim 12, wherein the liquid sample is selected from the group consisting of fruit juice, vegetable juice, milk and dairy products, raw and processed liquid foods, environmental samples, water, wastewater, samples taken by impingers and filtration, botanical liquid, industrial liquids, pharmaceutical liquids, and other liquid samples analyzed using enrichment-detection protocols.

20. The method of claim 1, wherein the diluting comprises addition to the sample, prior to transit of the sample to the second location, of a supplement selected from the group consisting of water, sugars, proteins, minerals, organics, vitamins and cofactors, antibiotics, dyes, indicators, buffers, agents to adjust the pH, water activity, nutritional contents, selective pressure to optimize the growth conditions for the target organism, and combinations thereof.

21. The method of claim 12, wherein the diluting comprises addition to the sample, prior to transit of the sample to the second location, of a supplement selected from the group consisting of water, sugars, proteins, minerals, organics, vitamins and cofactors, antibiotics, dyes, indicators, buffers, agents to adjust the pH, water activity, nutritional contents, selective pressure to optimize the growth conditions for the target organism, and combinations thereof.

22. A method for detection of a particular pathogen or other microbe, comprising:
obtaining a test sample at a first location, the sample being solid or semi-solid;
diluting, at the first location, the sample with liquid enrichment medium at a range of ratio of sample to diluent of about 1:0.1 to 1:2 (wt./vol.), or lesser dilution;
incubating the diluted or undiluted sample at an optimal temperature for the particular pathogen or other microbe to be detected in an incubator for testing in a second location that is an in-house or local lab; and
determining, at the in-house or local lab, by assaying the diluted incubated test sample, or a portion thereof, with an assay suitable to detect the particular pathogen or other microbe, whether the sample is contaminated with the particular pathogen or other microbe.

23. The method of claim 22, wherein the diluting comprises addition to the sample, prior to or during incubation, of a supplement selected from the group consisting of water, sugars, proteins, minerals, organics, vitamins and cofactors, antibiotics, dyes, indicators, buffers, agents to adjust the pH, water activity, nutritional contents, selective pressure to optimize the growth conditions for the target organism, and combinations thereof.

* * * * *